United States Patent
Jackson

(10) Patent No.: US 7,015,323 B2
(45) Date of Patent: Mar. 21, 2006

(54) THIOCARBAMATE INHIBITORS OF ALPHA-4 INTEGRINS

(75) Inventor: David Y. Jackson, San Bruno, CA (US)

(73) Assignee: Genentech, Inc., South San Francisco, CA (US)

( * ) Notice: Subject to any disclaimer, the term of this patent is extended or adjusted under 35 U.S.C. 154(b) by 92 days.

(21) Appl. No.: 10/850,002

(22) Filed: May 19, 2004

(65) Prior Publication Data

US 2004/0235750 A1 Nov. 25, 2004

Related U.S. Application Data

(60) Provisional application No. 60/472,072, filed on May 20, 2003.

(51) Int. Cl.
*C07D 265/30* (2006.01)
*C07D 241/04* (2006.01)
*C07D 498/08* (2006.01)
*C07D 221/20* (2006.01)

(52) U.S. Cl. .................. 544/105; 544/173; 544/176; 544/389; 544/383; 544/161; 546/244; 546/147; 546/15; 546/309; 548/531; 549/439

(58) Field of Classification Search ............... 544/173, 544/176, 389, 383, 105, 161; 546/244, 147, 546/15, 309; 548/531; 549/439; 514/237.5, 514/255.01, 423, 307, 278
See application file for complete search history.

(56) References Cited

U.S. PATENT DOCUMENTS

| 6,191,171 | B1 | 2/2001 | DeLaszlo et al. |
| 6,229,011 | B1 | 5/2001 | Chen et al. |
| 6,291,511 | B1 | 9/2001 | Durette et al. |
| 6,329,372 | B1 | 12/2001 | Head et al. |
| 6,403,584 | B1 | 6/2002 | de Laszlo et al. |
| 6,410,781 | B1 | 6/2002 | Konradi et al. |
| 6,469,047 | B1 | 10/2002 | Jackson et al. |
| 6,534,513 | B1 | 3/2003 | Porter et al. |
| 6,545,160 | B1 | 4/2003 | Konradi et al. |
| 6,677,339 | B1 | 1/2004 | Head et al. |
| 6,689,781 | B1 | 2/2004 | Konradi et al. |

FOREIGN PATENT DOCUMENTS

| EP | 1154987 | 11/2001 |
| EP | 1161416 | 12/2001 |
| EP | 1270547 | 1/2003 |
| WO | WO 98/46576 | 10/1998 |
| WO | WO 99/10312 | 3/1999 |
| WO | WO 99/36393 | 7/1999 |
| WO | WO 99/37618 | 7/1999 |
| WO | WO 9937618 A1 * | 7/1999 |
| WO | WO 99/50249 | 10/1999 |
| WO | WO 00/37444 | 6/2000 |
| WO | WO 01/21584 | 3/2001 |
| WO | WO 01/68586 | 9/2001 |

\* cited by examiner

*Primary Examiner*—Kamal A. Saeed
*Assistant Examiner*—Nyeemah Grazier
(74) *Attorney, Agent, or Firm*—David W Evans

(57) ABSTRACT

The invention provides novel thiocarbamate alpha-4 inhibitors of the general formula (I) that are resistant to metabolism having improved half-life and/or clearance properties compared to corresponding carbamate compounds wherein substituents L, X, Y, Z, $R^1$–$R^4$, m, n, o and p are as defined herein. Also provided are compositions comprising compounds of formula I and a carrier, diluent or excipient as well as methods of treating a disease or condition mediated by the binding interaction of alpha-4 integrins to its ligands such as inflammatory diseases.

18 Claims, No Drawings

THIOCARBAMATE INHIBITORS OF ALPHA-4 INTEGRINS

This application claims benefit of U.S. Provisional Application No. 60/472,072, filed on May 20, 2003.

FIELD OF THE INVENTION

The present invention relates to organic compounds useful for therapy and/or prophylaxis in a mammal, in particular tyrosine analogs treating conditions mediated by alpha-4 integrins.

BACKGROUND OF THE INVENTION

The integrins are α/β heterodimeric cell surface receptors involved in numerous cellular processes from cell adhesion to gene regulation. Hynes, R. O., Cell, 1992, 69:11–25; Hemler, M. E., Annu. Rev. Immunol., 1990, 8:365–368. Several integrins have been implicated in disease processes and have generated widespread interest as potential targets for drug discovery. Sharar, S. R. et al., Springer Semin. Immunopathol., 1995, 16:359–378. In the immune system integrins are involved in leukocyte trafficking, adhesion and infiltration during inflammatory processes. Nakajima, H. et al., J. Exp. Med., 1994, 179:1145–1154. Differential expression of integrins regulates the adhesive properties of cells and different integrins are involved in different inflammatory responses. Butcher, E. C. et al., Science, 1996, 272:60–66. The alpha4 integrins (i.e. alpha4beta1 (α4β1) and alpha4beta7 (α4β7)) are expressed primarily on monocytes, lymphocytes, eosinophils, basophils, and macrophages but not on neutrophils. Elices, M. J. et al., Cell, 1990, 60:577–584. The primary ligands for α4 integrins are the endothelial surface proteins mucosal addressin cell adhesion molecule (MAdCAM) and vascular cell adhesion molecule (VCAM) with lower affinity. Makarem, R. et al., J. Biol. Chem., 1994, 269:4005–4011. The binding of the α4β7 or α4β1 to MAdCAM and/or VCAM expressed on high endothelial venules (HEVs) at sites of inflammation results in firm adhesion of the leukocyte to the endothelium followed by extravasation into the inflamed tissue. Chuluyan, H. E. et al., Springer Semin. Immunopathol., 1995, 16:391–404.

Monoclonal antibodies directed against α4β1, α4β7, MAdCAM or VCAM have been shown to be effective modulators in animal models of chronic inflammatory diseases such as asthma (Laberge, S. et al., Am. J. Respir. Crit. Care Med., 1995, 151:822–829.), rheumatoid arthritis (R A; Barbadillo, C. et al., Springer Semin. Immunopathol., 1995, 16:375–379), colitis (Viney et al, J. Immunol., 1996, 157: 2488–2497) and inflammatory bowel diseases (IBD; Podalski, D. K., N. Eng. J. Med., 1991, 325:928–937; Powrie, F. et al., Ther. Immunol., 1995, 2:115–123). While antibodies can be effective inhibitors of alpha-4 integrins, they are inherently difficult and expensive to manufacture. They are also not orally bioavailable and inconveniently require administration by injection from a physician or other qualified healthcare giver.

In an attempt to find more convenient treatments, many types of small molecules have been made to inhibit binding interaction of alpha-4 integrins with their ligands, a promising example of which are phenylalanine derivatives such as those described in U.S. Pat. No. 6,410,781, U.S. Pat. No. 6,229,011, U.S. Pat. No. 6,329,372, EP 1,270,547, WO 01/68,586 and WO 99/36,393. A particular type of potent alpha-4 integrin inhibitor are tyrosine compounds described in U.S. Pat. No. 6,469,047 which are derivatized at the hydroxyl group to form a carbamate. A representative compound disclosed in U.S. Pat. No. 6,469,047 is incorporates a tyrosine residue conjugated to a morpholino heterocycle by way of a carbamate linkage. The carbamates are potent inhibitors of alpha-4 integrins but have been shown to metabolize rapidly in vivo yielding a phenoxy metabolite and thereby having a short half life.

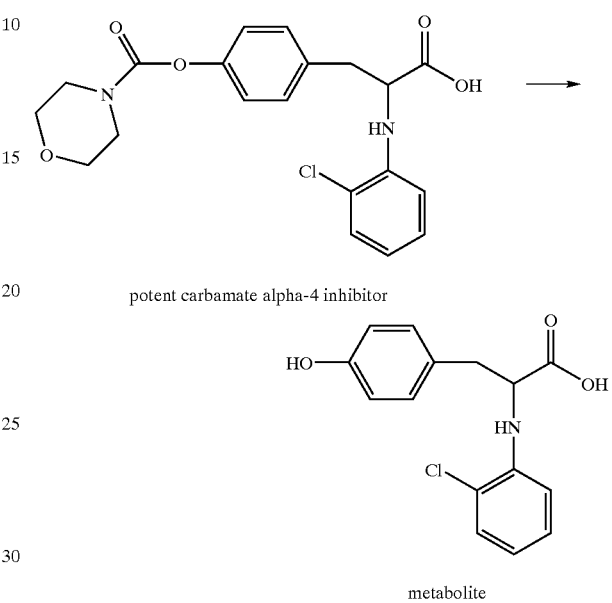

potent carbamate alpha-4 inhibitor metabolite

Accordingly, there remains a need for small molecule inhibitors of alpha-4 integrins that are resistant to metabolism having prolonged in vivo half-life.

SUMMARY OF THE INVENTION

In one aspect of the present invention there is provided novel thiocarbamate alpha-4 inhibitors of formula (I) that are resistant to metabolism having improved half-life and/or clearance properties compared to corresponding carbamate compounds:

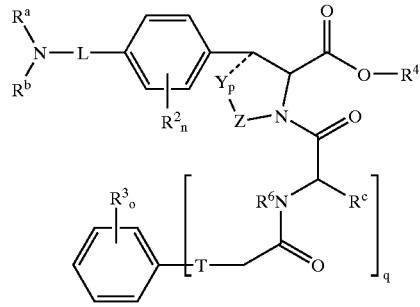

wherein
q is 0 or 1;
T is O, $CHR^6$, $NR^6$, S, SO, $SO_2$, —$NR^6C(O)$—, —$C(O)NR^6$—;
$R^a$ and $R^b$ are each independently hydrogen, alkyl, alkoxy, a carbocycle, a heterocycle, optionally substituted with halogen, hydroxy, amino, carboxyl, nitro, cyano, a carbocycle or a heterocycle; and one to three carbon atoms of said alkyl and alkoxy groups are optionally replaced with carbonyl, $NR^6$, O, S, SO or $SO_2$; or $R^a$ and $R^b$ together with the nitrogen to which they are attached may form a heterocycle or heteroaryl group substituted with 0–4 $R^1$ substituents;

$R^c$ is H, alkyl, optionally substituted with hydroxy, halogen, alkoxy, amino, a carbocycle or a heterocycle; and a carbon atom of said alkyl is optionally replaced with carbonyl, $NR^6$, O, S, SO or $SO_2$;

L is —C(S)—O— or —C(O)—S—;

X is O, $NR^5$, $CR^1R^6$, S, SO or $SO_2$;

Y is $CH_2$ or absent when p is 0;

Z is H or lower alkyl, or when p is 1 then Z and Y together with the atoms from which they depend form a 5 member saturated or partially unsaturated 5 or 6 member heterocycle;

$R^1$ in each instance is independently selected from the group consisting of hydroxy, amino, amidine, guanidine, carboxyl, nitro, cyano, thiol, alkyl, alkoxy a carbocycle and a heterocycle wherein said alkyl and alkoxy groups are optionally substituted with one or more hydroxyl, halogen, amino, amidine, guanidine, carboxyl, nitro, cyano, carbocycle or heterocycle; and one to three carbon atoms of said alkyl and alkoxy groups are optionally replaced with carbonyl, $N R^6$, O, S, SO or $SO_2$; and said carbocycle and heterocycle group is optionally substituted with one or more hydroxyl, halogen, amino, amidine, guanidine carboxyl, nitro, cyano, alkyl, alkoxy or haloalkyl;

or two $R^1$ substituents together with the atoms from which they depend form a fused or bridged heterocycle optionally substituted with one or more hydroxyl, halogen, amino, amidine, guanidine carboxyl, nitro, cyano, alky, alkoxy or haloalkyl;

$R^2$ and $R^3$ in each instance are independently selected from the group consisting of hydroxy, amino, amidine, guanidine, carboxyl, nitro, cyano, thiol, alkyl, alkoxy, a carbocycle and a heterocycle wherein said alkyl and alkoxy groups are optionally substituted with one or more hydroxyl, halogen, amino, amidine, guanidine, carboxyl, nitro, cyano, alkoxy, carbocycle or heterocycle; and one to three carbon atoms of said alkyl group is optionally replaced with carbonyl, $NR^6$, O, S, SO or $SO_2$; and said carbocycle and heterocycle group is optionally substituted with one or more hydroxyl, halogen, amino, amidine, guanidine, carboxyl, nitro, cyano, alkyl, alkoxy or haloalkyl;

$R^4$ is H, alkyl, a carbocycle or heterocycle wherein said alkyl is optionally substituted with a carbocycle or heterocycle and said alkyl, carbocycle and heterocycle are optionally substituted with lower alkyl, halogen, hydroxyl, alkoxy, haloalkyl or amino;

$R^5$ in each instance is independently selected from the group consisting of H, alkyl, a carbocycle and a heterocycle wherein said alkyl group is optionally substituted with one or more hydroxyl, halogen, amino, amidine, guanidine, carboxyl, nitro, cyano, alkoxy carbocycle or heterocycle; and one to three carbon atoms of said alkyl group is optionally replaced with carbonyl, $NR^6$, O, S, SO or $SO_2$; and said carbocycle and heterocycle group is optionally substituted with one or more hydroxyl, halogen, amino, amidine, guanidine carboxyl, nitro, cyano, alkyl, alkoxy or haloalkyl;

$R^6$ in each instance is independently H, alkyl or a carbocycle;

m, n, and o are each independently 0–4;

p is 0 or 1; and salts and solvates thereof.

In another aspect of the invention, there are provided compositions comprising compounds of formula I and a carrier, diluent or excipient.

In another aspect of the invention, there are provided methods of treating a disease or condition mediated by the binding interaction of alpha-4 integrins to its ligands, comprising administering to a mammal an effective amount of the compound of formula I.

DETAILED DESCRIPTION OF THE PREFERRED EMBODIMENTS

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion is preferably a saturated hydrocarbon chain, however also includes unsaturated hydrocarbon carbon chains such as "alkenylamino" and "alkynylamino. Examples of alkyl groups include methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$–$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one (preferably), two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Preferred substituted alkyls are substituted methyls e.g. a methyl group substituted by the same substituents as the "substituted $C_n$–$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" denotes the group —C(NH)—NHR wherein R is H or alkyl or aralkyl. A preferred amidine is the group —NH—C(NH)—$NH_2$.

"Amino" denotes primary (i.e. —$NH_2$), secondary (i.e. —NRH) and tertiary (i.e. —NRR) amines. Preferred secondary and tertiary amines are alkylamine, dialkylamine, arylamine, diarylamine, aralkylamine and diaralkylamine. Particular preferred secondary and tertiary amines are as methylamine, ethylamine, propylamine, isopropylamine, phenylamine, benzylamine dimethylamine, diethylamine, dipropylamine and disopropylamine.

The term "amidine" denotes the group —C(NH)NHR wherein R is H or alkyl or aralkyl. Preferred amidine is the group —C(NH)$NH_2$.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Preferred aryl groups include phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]) and most preferred phenyl. Substituted phenyl or substituted aryl denotes a phenyl group or aryl group substituted with one, two, three, four or five, preferably 1-2, 1-3 or 1-4 substituents chosen, unless otherwise specified, from halogen (F, Cl, Br, I), hydroxy, protected hydroxy, cyano, nitro, alkyl (preferably $C_1$–$C_6$ alkyl), alkoxy (preferably $C_1$–$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene (CH$_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl) phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy4-benzyloxyphenyl, 3-methoxy-4-(1-chloromethyl)benzyloxyphenyl, 3-ethoxyphenyl, 4-(isopropoxy)phenyl, 4-(t-butoxy) phenyl, 3-ethoxy4-methoxyphenyl and the like; 3- or 4-trifluoromethylphenyl; a mono- or dicarboxyphenyl or (protected carboxy)phenyl group such 4-carboxyphenyl,; a mono- or di(hydroxymethyl)phenyl or (protected hydroxymethyl)phenyl such as 3-(protected hydroxymethyl) phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy4-benzyloxy-5-methyl-6-phenyl sulfonylamino. Preferred substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any, preferably 1, 2 or 3, of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms and preferably 3 to 7 carbon atoms which may be saturated or unsaturated, aromatic or non-aromatic. Preferred saturated carbocyclic groups include cyclopropyl, cyclobutyl, cyclopentyl and cyclohexyl groups and more preferred are cyclopropyl and cyclohexyl and most preferred is cyclohexyl. Preferred unsaturated carbocycles are aromatic e.g. aryl groups as previously defined, the most preferred being phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl) ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", 2nd ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" denotes the group —NH—C(NH)—NHR wherein R is H or alkyl or aralkyl. Preferred guanidine is the group —NH—C(NH)—NH$_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, acetoxy, carbamoyloxy, trifluoro, chloro, carboxy, bromo and iodo groups. Further examples of these groups are found in T. W. Greene and P. G. M. Wuts, "Protective Groups in Organic Synthesis", 2nd ed., John Wiley & Sons, Inc., New York, N.Y., 1991, chapters 2–3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen) and preferably 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, SO$_2$), and any nitrogen heteroatom may optionally be quaternized. Preferred non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Preferred 5-membered heterocycles containing a sulfur or oxygen atom and one to three nitrogen atoms include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. Preferred 5-membered ring heterocycles containing 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. Preferred benzo-fused 5-membered heterocycles are benzoxazol-2-yl, benzthiazol-2-yl and benzimidazol-2-yl. Preferred 6-membered heterocycles contain one to three nitrogen atoms and optionally a sulfur or oxygen atom, for example pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a preferred group. Substituents for optionally substituted heterocycles, and further examples of the 5- and 6-membered ring systems discussed above can be found in W. Druckheimer et al., U.S. Pat. No. 4,278,793.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and preferably at least one heteroatom is nitrogen (*Lang's Handbook of Chemistry*, supra). Included in the definition are any bicyclic groups where any of the above heteroaryl rings are fused to a benzene ring. Heteroaryls in which nitrogen or oxygen is the heteroatom are preferred. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particularly preferred group of "heteroaryl" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5- dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"Inhibitor" means a compound which reduces or prevents the binding of alpha-4 integrins to their ligands, for example alpha4beta1 integrin to VCAM-1 ligand alpha4beta7 integrin to MAdCAM-1 ligand or which reduces or prevents the initiation of a cellular response mediated by the binding interaction of the alpha-4 integrins to their ligands.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The present invention provides compounds having the general formula I:

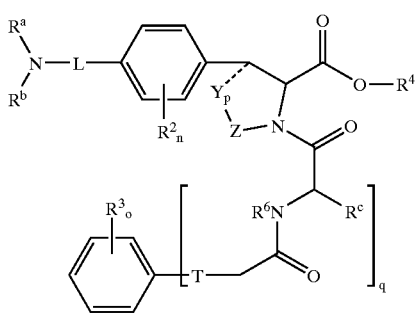

wherein q, T $R^a$–$R^c$, L, X, Y, Z, $R^2$–$R^4$, m, n, o, p are as defined herein.

q is 0 or 1. In a particular embodiment q is 0. In another particular embodiment q is 1.

T is O, $CHR^6$, $NR^6$, S, SO, $SO_2$, —$NR^6C(O)$—, —$C(O)NR^6$—. I a preferred embodiment T is O or —$C(O)NR^6$— and most preferably O.

$R^a$ and $R^b$ are each independently hydrogen, alkyl, alkoxy, a carbocycle, a heterocycle, optionally substituted with halogen, hydroxy, amino, carboxyl, nitro, cyano, a carbocycle or a heterocycle. One to three carbon atoms of said alkyl and alkoxy groups are optionally replaced with carbonyl, $NR^6$, O, S, SO or $SO_2$ in the same manner as described for $R^1$. Preferred groups formed by $R^a$ and $R^b$ with the nitrogen atom from which they depend are:

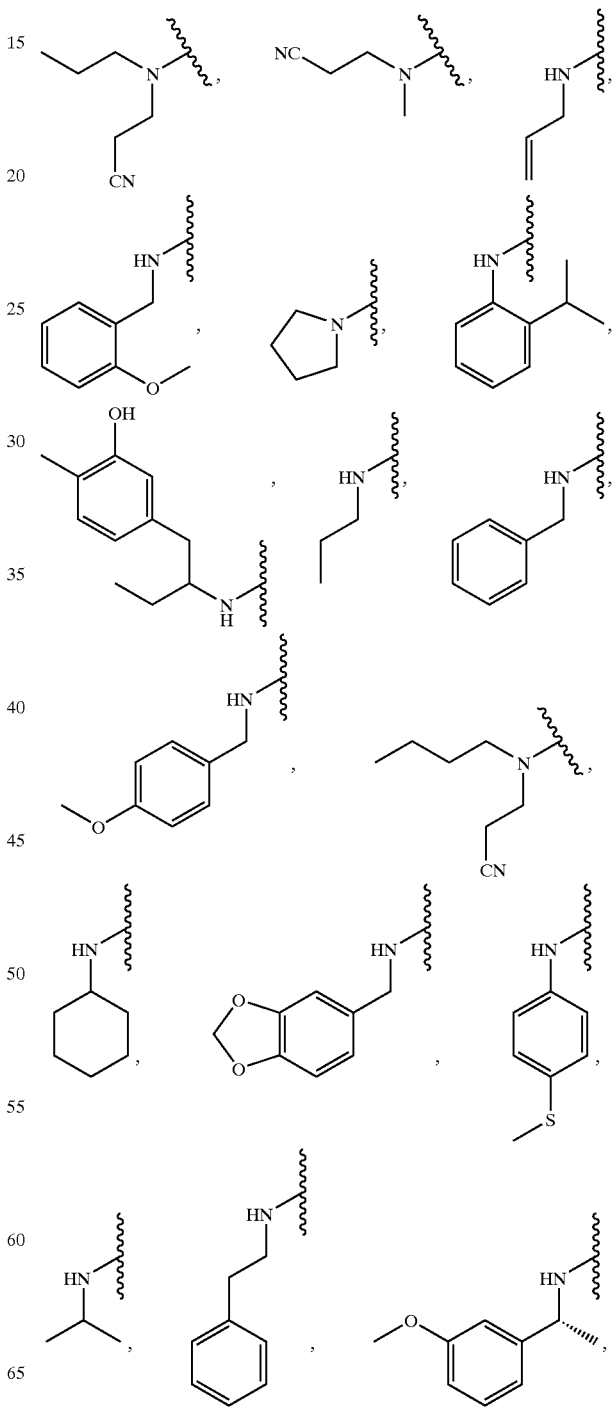

-continued

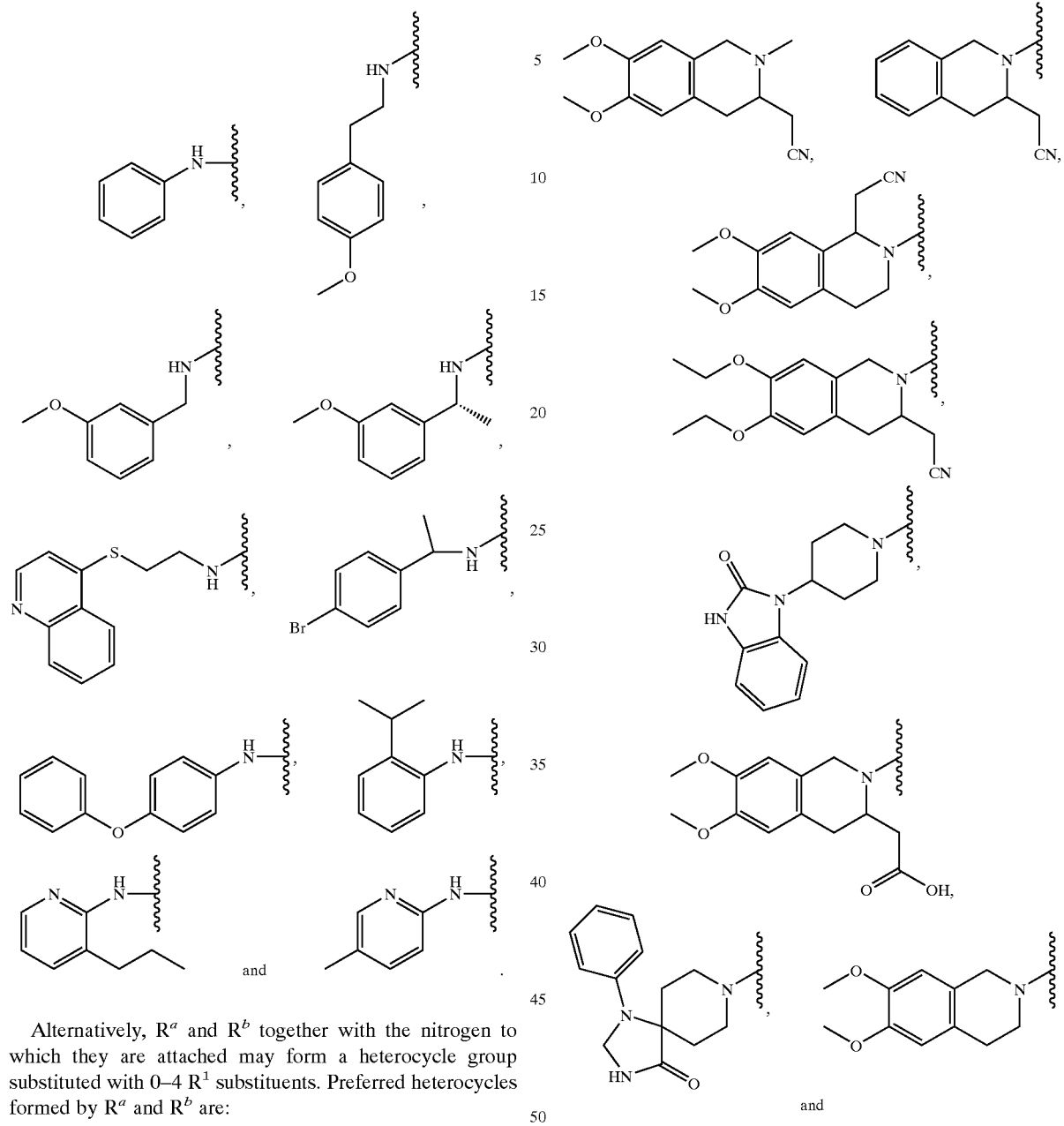

Alternatively, $R^a$ and $R^b$ together with the nitrogen to which they are attached may form a heterocycle group substituted with 0–4 $R^1$ substituents. Preferred heterocycles formed by $R^a$ and $R^b$ are:

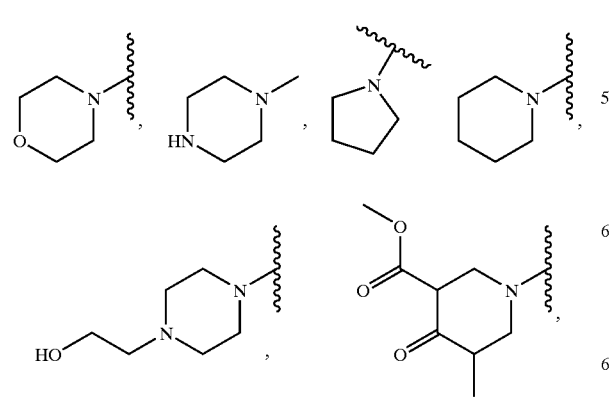

$R^c$ is H, alkyl, optionally substituted with hydroxy, halogen, alkoxy, amino, a carbocycle or a heterocycle. One to three carbon atoms of said alkyl are optionally replaced with carbonyl, $NR^6$, O, S, SO or $SO_2$ in the same manner as described for $R^1$ below. In a preferred embodiment $R^c$ is an amino acid sidechain, preferably a sidechain of a naturally occurring amino acid. In a particularly preferred embodiment $R^6$ is H or the amino acid side chain of glycine, valine, leucine or isoleucine and most preferably leucine. In a particularly preferred embodiment, q is 1 and $R^c$ is a leucine side chain while T is O, $R^3$ is t-butyl and o is 1. More preferably q is 1 and $R^c$ is a leucine side chain while T is O, $R^3$ is t-butyl, o is 1, $R^a$ and $R^b$ form a morpholino ring, L is —C(S)—O—, Z is H, Y is absent, p is 0 and $R^4$ and $R^6$ are both H.

L is —C(S)—O— or —C(O)—S— thereby forming a thiocarbamate linkage. In a preferred embodiment L is —C(S)—O—.

Y is $CH_2$ or is absent when p is 0. In a preferred embodiment p is 0 and Y is absent.

Z is H or lower alkyl, or when p is 1 then Z and Y together with the atoms from which they depend form a 5 member saturated or partially unsaturated 5 or 6 member heterocycle. In a particular embodiment Z and Y are both $CH_2$ and p is 1 thereby forming a pyrrolidine ring and constraining rotation of the tyrosine residue. In a preferred embodiment Z is H or methyl and most preferably H while p is 0 and Y is absent.

$R^2$ and $R^3$ in each instance are independently selected from the group consisting of hydroxy, amino, amidine, guanidine, carboxyl, nitro, cyano, thiol, alkyl, alkoxy, a carbocycle and a heterocycle. The alkyl and alkoxy groups of $R^2$ and $R^3$ are optionally substituted with one or more hydroxyl, halogen, amino, amidine, guanidine, carboxyl, nitro, cyano, alkoxy, carbocycle or heterocycle. Further, one to three carbon atoms of said alkyl group is optionally replaced with carbonyl, $NR^6$, O, S, SO or $SO_2$ in the same manner as described for $R^1$ below. The carbocycle and heterocycle groups of $R^2$ and $R^3$ are optionally substituted with one or more hydroxyl, halogen, amino, amidine, guanidine, carboxyl, nitro, cyano, alkyl, alkoxy or haloalkyl. In a particular embodiment, $R^2$ is in each instance halogen, alkyl, alkoxy, aryl or aryloxy. In a particularly preferred embodiment, n is 1 and $R^2$ is adjacent to the thiocarbamate linkage and is selected from the group consisting of Cl, I, methyl, methoxy and phenyl. In another particularly preferred embodiment n is 0 and $R^2$ is absent. In a particular embodiment, $R^3$ is halogen, nitro, carboxyl or alkylsulfonyl optionally substituted with halogen, hydroxyl or alkoxy. In another particular embodiment $R^3$ is Cl, nitro, carboxyl, —$NHSO_2CF_3$, —$NHC(O)CF_3$ or 4-methyl-phenyl. In a particularly preferred embodiment o is 1 and $R^3$ is Cl adjacent to the amide linkage.

$R^4$ is H, alkyl, a carbocycle or heterocycle wherein said alkyl is optionally substituted with a carbocycle or heterocycle and said alkyl, carbocycle and heterocycle are optionally substituted with lower alkyl, halogen, hydroxyl, alkoxy, haloalkyl or amino. In a preferred embodiment $R^4$ is H, alkyl or aralkyl. In a particularly preferred embodiment $R^4$ is methyl, ethyl, isobutyl or benzyl and more preferably ethyl. In another particularly preferred embodiment $R^4$ is H.

$R^6$ in each instance is independently H, alkyl or a carbocycle. In a preferred embodiment, $R^6$ is H.

and o are each independently 0–4. In a particular embodiment m and n are both 0–1 and o is 1–2. More preferably, m and n or both 0 and o is 1.

p is 0 or 1. In a preferred embodiment p is 1 and Y is $CH_2$ thereby forming a heterocycle, more preferably a pyrrolidine. In another preferred p is 0 and Y is absent.

In a particular embodiment, compounds of the invention have the general formula II

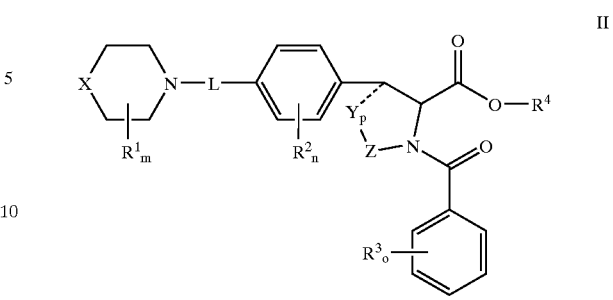

wherein L, Y, Z, $R^2$–$R^4$, n, o, p are as defined above and m, X, $R^1$ and $R^5$ are as defined herein below.

m is 0–4 preferably 0–4 2 more preferably 0–1 and most preferably 0. In a particular embodiment m and o are both 0–1. In another particular embodiment m and n are both 0 and o is 1.

X is O, $NR^5$, $CR^1R^6$, S, SO or $SO_2$. In a particular embodiment X is $CR^1R^6$. In another particular embodiment X is S. In another embodiment X is $SO_2$. In a preferred embodiment X is SO. In another preferred embodiment X is $NR^5$ wherein $R^5$ is as defined below. In a most preferred embodiment X is O thereby forming a morpholino heterocycle.

$R^1$ in each instance is independently selected from the group consisting of hydroxy, amino, amidine, guanidine, carboxyl, nitro, cyano, thiol, alkyl, alkoxy a carbocycle and a heterocycle. The carbocycle and heterocycle group of $R^1$ is optionally substituted with one or more, preferably 1–3, hydroxyl, halogen, amino, amidine, guanidine carboxyl, nitro, cyano, alkyl, alkoxy or haloalkyl. The alkyl and alkoxy groups of $R^1$ are optionally substituted with one or more, preferably 1–3, hydroxyl, halogen, amino, amidine, guanidine, carboxyl, nitro, cyano, carbocycle or heterocycle substituents. Further, one to three carbon atoms of said alkyl group (as well as any pending hydrogen atoms, e.g. methylene) are optionally replaced with carbonyl C(O), $NR^6$, O, S, SO or $SO_2$. In a preferred embodiment a carbon atom in an alkyl chain is replaced to form an alkanoyl, ketone or aldehyde group. In another preferred embodiment, a carbon atom in an alkyl chain is replaced with $NR^6$ to form an amine, aminoalkyl or mono- or di-alkylaminoalkyl. In another preferred embodiment, a carbon atom is replaced with O to form an alkoxy, alkoxyalkyl (ether) or hydroxyalkyl. In another preferred embodiment, a carbon atom in an alkyl chain is replaced with S to form an alkylthio, thioether or thiolalkyl. In another embodiment, two or more adjacent carbon atoms in an alkyl chain are replaced with —$NR^6$—C(O)—, —C(O)—$NR^6$—, —$NR^6$—SO, —SO—$NR^6$—, —$NR^6$—$SO_2$— or —$SO_2$—$NR^6$—. In a preferred embodiment, two or more carbon atoms in an alkyl chain are replaced to form amide groups —$NR^6$—C(O)-alkyl, —C(O)$NR^6$-alkyl; or alkylsulfonyl groups —$NR^6$—$SO_2$-alkyl, —$SO_2$—$NR^6$-alkyl, —N—$(SO_2$-alkyl$)_2$ or —$SO_2$—N(alkyl)$_2$. Particularly preferred alkylsulfonyl groups are —NH—$SO_2$-Me, —NH—$SO_2$-Et, —NH—$SO_2$—Pr, —NH—$SO_2$-iPr, —N—$(SO_2$—Me$)_2$ and —N—$(SO_2$—Bu$)_2$.

In a preferred embodiment $R^1$ in each instance is H; or alkyl, aryl, heteroaryl each optionally substituted with hydroxyl, halogen amino or cyano. In a particularly preferred embodiment $R^1$ is H, methyl, ethyl, isopropyl, cyanomethyl. In another particularly preferred embodiment m is 0 and R¹ is absent. In another particularly preferred embodiment m is 1 and R¹ is methyl adjacent to the thiocarbamate nitrogen atom.

In another embodiment, two R¹ substituents together with the atoms from which they depend form a fused or bridged heterocycle optionally substituted with one or more hydroxyl, halogen, amino, amidine, guanidine carboxyl, nitro, cyano, alky, alkoxy or haloalkyl. A preferred fused heterocycle formed by adjacent R¹ substituents is 1,2,3,4-tetrahydroisoquinoline which is optionally substituted with one or more alkoxy and preferably 6,7,-dimethoxy substituted. Preferred bridged heterocycles formed by non-adjacent R¹ substituents are 2-Oxa-5-azabicyclo[2.2.1]heptane and 2,5-Diazabicyclo[2.2.1]heptane, the latter optionally N-substituted with an acyl group such as acetyl.

R⁵ in each instance is independently selected from the group consisting of H, alkyl, a carbocycle and a heterocycle. The carbocycle and heterocycle groups of R⁵ are optionally substituted with one or more hydroxyl, halogen, amino, amidine, guanidine carboxyl, nitro, cyano, alkyl, alkoxy or haloalkyl. The alkyl group of R⁵ is optionally substituted with one or more hydroxyl, halogen, amino, amidine, guanidine, carboxyl, nitro, cyano, alkoxy, carbocycle or heterocycle. Further, one to three carbon atoms of said alkyl group is optionally replaced with carbonyl, NR⁶, O, S, SO or SO₂ in the same manner as described for R¹. In a particular embodiment R⁵ is H, alkyl and alkanoyl, optionally substituted with hydroxyl, halogen, amino or aryl. In a particularly preferred embodiment R⁵ is H, methyl, ethyl or acetyl and in a more preferred embodiment H or acetyl.

Compounds of the invention contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention. Preferably, compounds of the invention have an S configuration at the alpha carbon of the tyrosine residue or the naturally occurring configuration thereof.

The invention also encompasses prodrugs of the compounds described above. Suitable prodrugs include known amino-protecting and carboxy-protecting groups which are released, for example hydrolyzed, to yield the parent compound under physiologic conditions. A preferred class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. Preferably the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT application WO9846576) the contents of which are incorporated herein by reference in their entirety.

Particularly preferred compounds of formula I and II are:

1

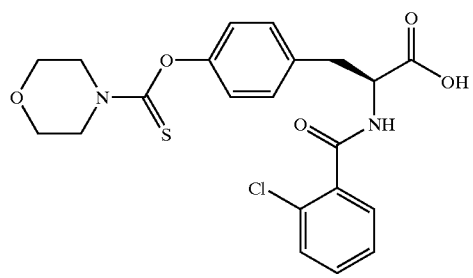

2

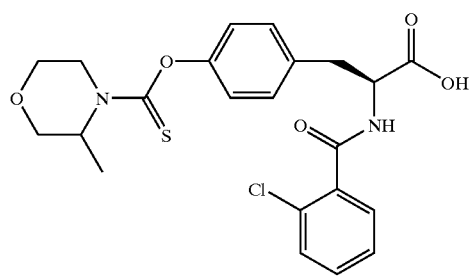

3

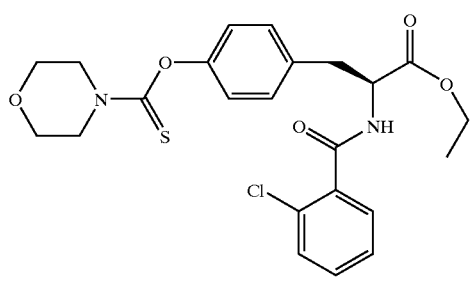

4

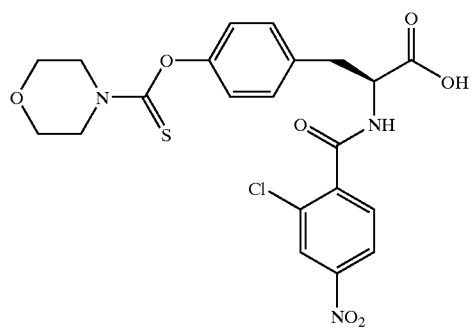

-continued
5
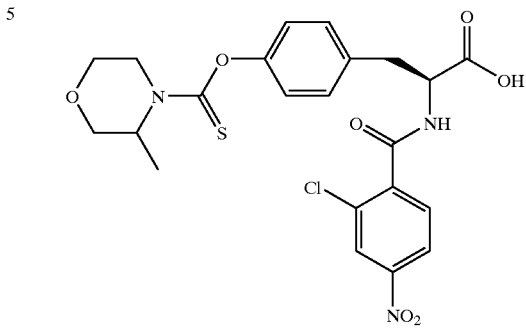
6
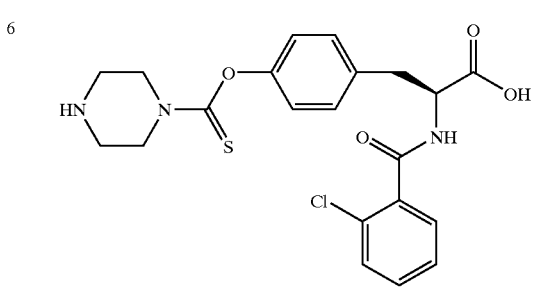
7
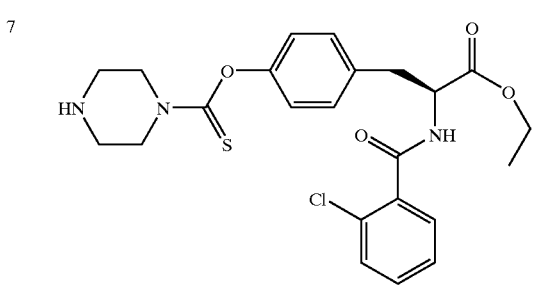
8
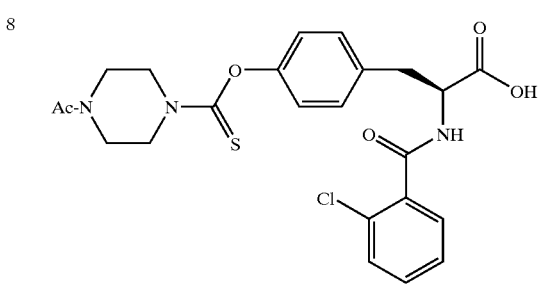
9
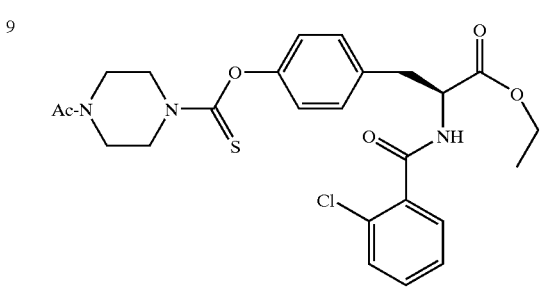
-continued
10
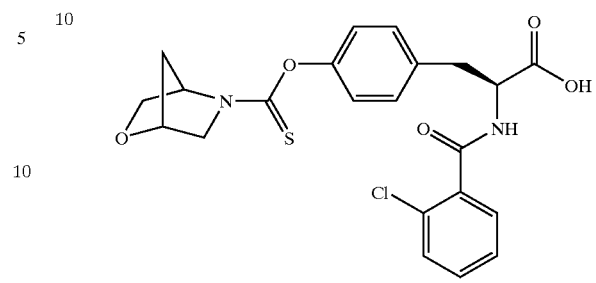
11
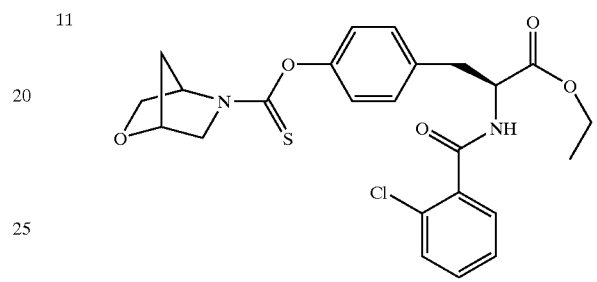
12
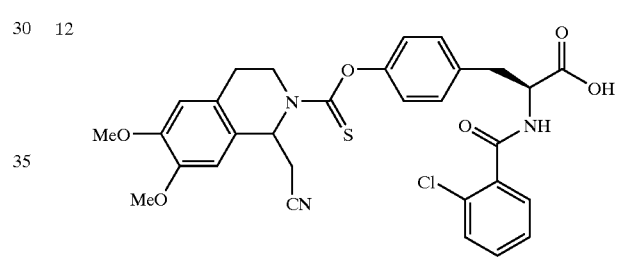
and
13
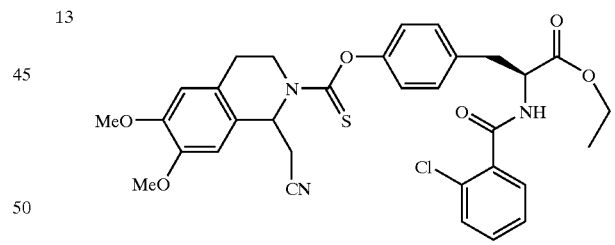
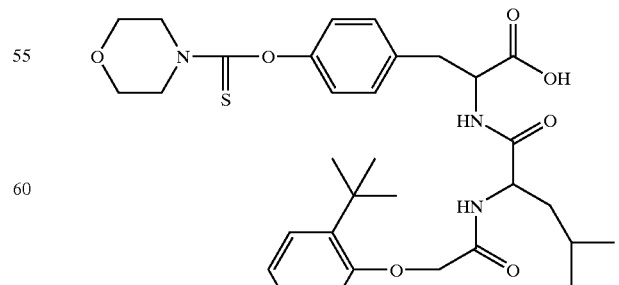

Synthesis

Compounds of the invention are prepared using standard organic synthetic techniques from commercially available starting materials such as those described in U.S. Pat. No. 6,469,047 which in its entirety is incorporated herein by reference. While various synthetic schemes can be employed, the compounds of formula I in which L is —C(S)—O— may be prepared starting from a tyrosine ester according to the following scheme

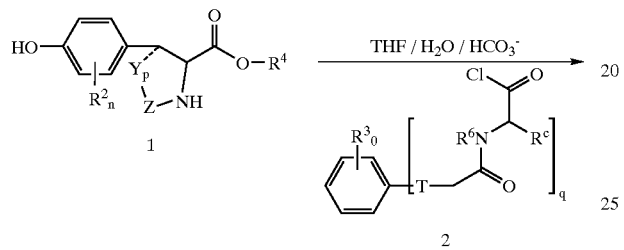

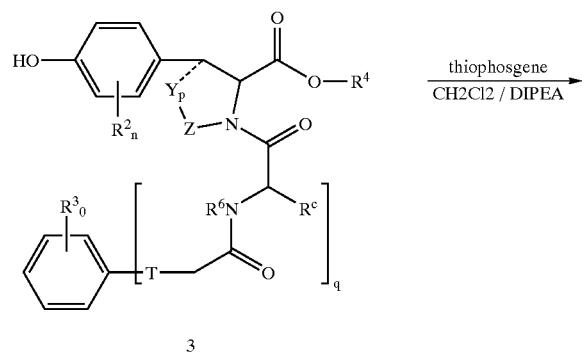

in which the starting tyrosine ester 1 is reacted with an acyl halide or acyl anhydride, e.g. acyl chloride 2, in THF with mild base, e.g. sodium bicarbonate, to give intermediate 3. Intermediate 3 is then reacted with thiophosgene in methylenedichloride with diisopropylethylamine to give thiochloroformate 4 which is reacted with amine 5 in methylenedichloride and diiodopropylethylamine to give thiocarbamate 6 ester. Conversion of the ester to a carboxylic acid is easily performed by saponification with an alkalimetal hydroxide such as lithium, sodium, or potassium hydroxide. The starting tyrosine, acyl chloride intermediate 2 and amine intermediate 3 are either commercially available or are prepared from starting materials that commercially available employing established synthetic techniques.

Numerous starting tyrosine derivatives are commercially available or can be readily synthesized using standard chemical reactions. An example of the synthesis of a particular intermediate useful in preparing compounds of the invention is:

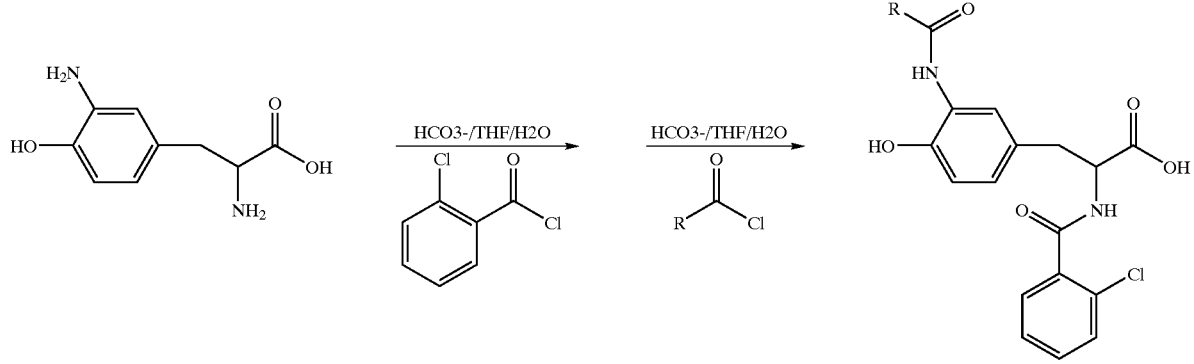

In this scheme, R may be any suitable group which is non-reactive under the reaction conditions. Examples of suitable R groups include substituted and unsubstituted alkyl, aryl, arylalkyl, etc. Additional compounds of the invention can then be prepared by acylating the phenyl hydroxy group with an activated thiocarbonyl to form a thiocarbamate as described herein.

Solid phase reaction chemistry provides a convenient method for synthesizing the compounds of the invention. FMOC- or BOC- protected amino acids and derivatives thereof are readily available and can be used as starting materials in the synthesis of the compounds of the invention. The protected amino acid is initially attached to a synthetic resin having an available coupling group, such as an available hydroxy (e.g. benzyloxy resin beads). Coupling is achieved using known chemical reactions, e.g. condensation reactions using for example DIPC or DMAP, to attach the amino acid to the solid support. Any known coupling reactions and resin surfaces may be used. The amino nitrogen is then deprotected using, for example, a weak base such as piperidine or other suitable base. The free amino group can then be reacted with an activated ester such a HBTU or HOBT ester of a suitable group such as 2-chlorobenzoic acid to form the desired N-substituted tyrosine intermediate.

Tyrosine intermediates are further reacted to form thiocarbamates, using known chemistry. For example, the hydroxy group can be reacted with a thiocarbonyl synthon such as thiophosgene, followed by the desired primary or secondary amine, e.g. cyclic secondary amine, to form thiocarbamates as shown in the reaction scheme below.

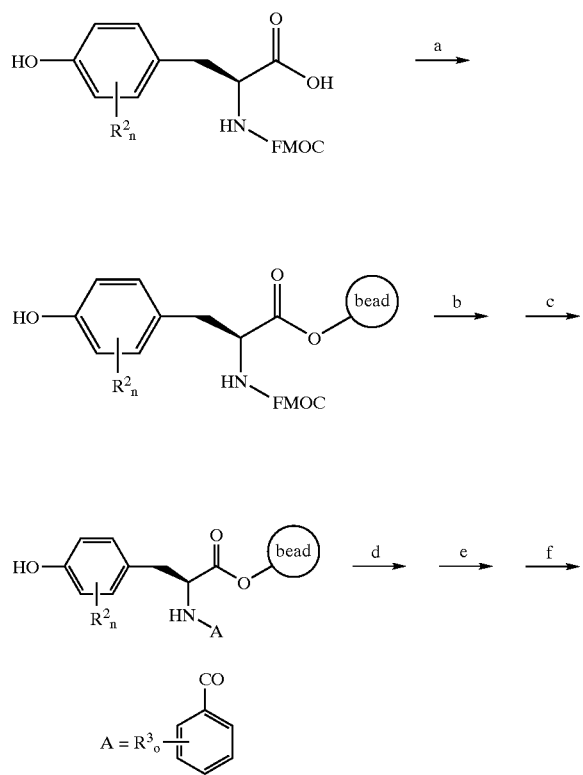

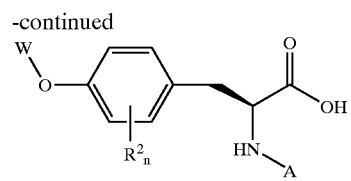

In this scheme, a=DIPC cat./DMAP; b=20% piperidine/DMA or DMF; c=a substituted benzoic acid/HBTU or other amide coupling agent/TEA or other weak base; d=primary or secondary amine; e=TFA/triethylsilane, for example.

Compounds of formula I may be synthesized manually via solid phase synthesis on p-alkoxybenzyl alcohol resin (Advanced Chemtech, USA) as shown above. Commercially available FMOC protected tyrosine or other tyrosine analogs may be purchased from BACHEM Ca., Advanced ChemTech U.S.A., or Calbiochem Corp. (Ca.) or prepared from commercially available reagents. Typically 1 mmol of FMOC-tyrosine (or tyrosine analog) is added to 1 g of p-alkoxybenzylalcohol resin in 50 mL dichloromethane. Diisopropylcarbodiimide (DIPC, 1 mmol) is added followed by catalytic dimethylaminopyridine (DMAP, 0.1 mmol) and the resulting mixture is stirred under nitrogen at 20 C for 4 hours. The resin is then washed with dichloromethane and dimethylacetamide (DMA) and the FMOC group is removed via mixing with 20% piperidine in DMA for fifteen minutes. The resin is then washed three times with DMA to remove excess piperidine.

Ortho-chlorobenzoic acid (2 mmol) or other substituted benzoic acid is mixed with HBTU (2 mmol) or other suitable activating agent in 20 mL of DMA and added to the previously washed resin. N-methylmorpholine or triethylamine (4 mmol) is added and the mixture sparged with nitrogen for 30 minutes. The resin is washed with dichloromethane and treated with 2 mmol of thiophosgene and 0.05 mmol DMAP in 20 mL of DMA for 1 h. Excess reagents are washed away and 2 mmol of morpholine or other substituted amine RaRb-NH in 20 mL dichloromethane is added. The mixture is sparged overnight at room temperature and washed with dichloromethane.

Treatment with TFA containing 5% triethylsilane for 1 hour affords the crude product. The crude material is extracted from the resin by stirring with 100 mL of 2:1 $H_2O/CH_3CN$ for 5 minutes followed by filtration to remove the resin. The crude filtrate is lyophilized and purified by preparative reverse phase $C_{18}$ HPLC ($CH_3CN/H_2O$ gradient, 0.1% TFA) to afford purified material. Pure fractions are characterized by electrospray ionization mass spectrometry (Sciex API100) and proton NMR, lyophilized to dryness and resuspended in DMSO at 10 mM just prior to biological assay. Serial dilutions at 0.5 mM are titrated into an ELISA format assay and the $IC_{50}$ for each compound may then be determined.

Alternatively, compounds of formula I can be synthesized in three steps via solution phase chemistry starting with commercially available (L)-tyrosine or tyrosine analogs having substituents at $R^2$. A general synthesis is depicted below. This type of synthesis is amenable to scale up and for introducing ester prodrugs at $R^4$.

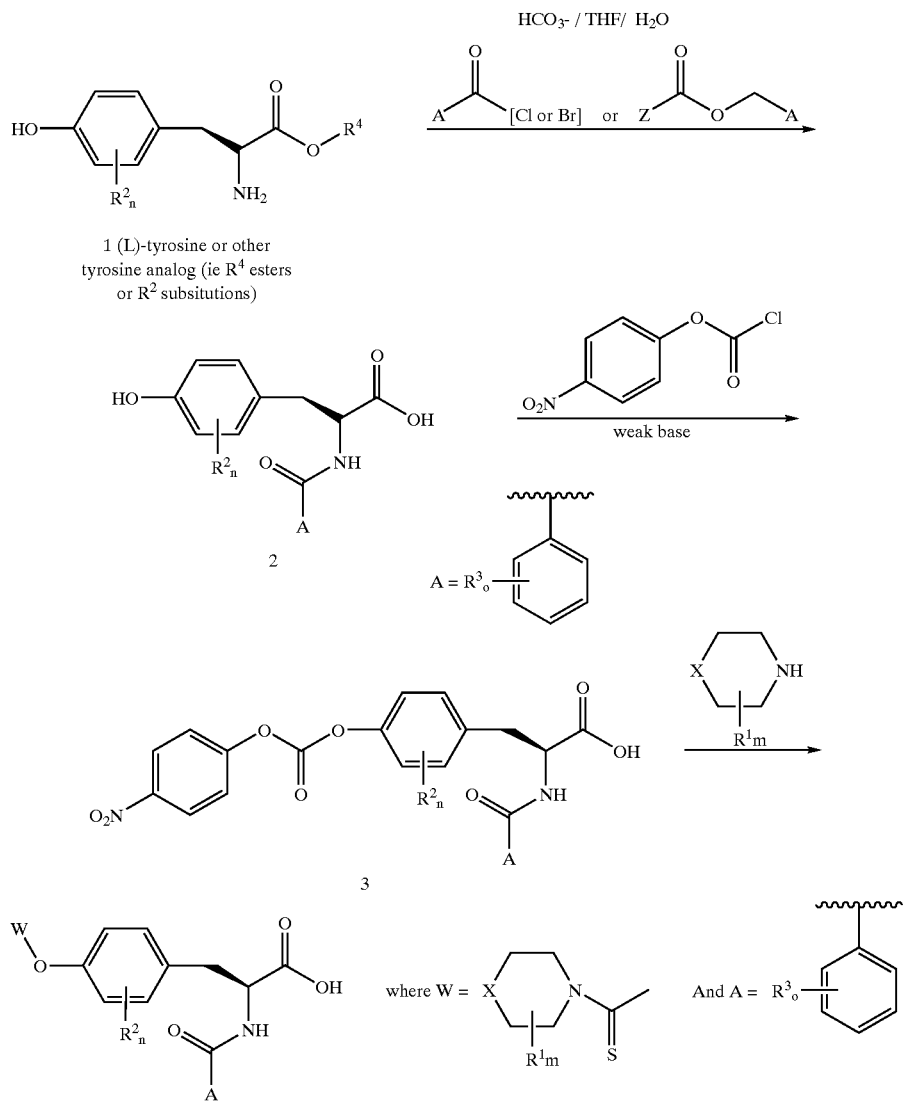

Typically, 100 mmols of (L)-tyrosine or similar tyrosine analog is dissolved in 500 mL THF/H$_2$O (1:1) and 300 mmols of sodium bicarbonate is added followed by 110 mmols (1.1 eq.) of a suitable benzoyl chloride or anhydride of general structure A-COCl. The solution is stirred at room temperature for 1 h. The mixture is concentrated via rotary evaporation and acidified to pH<3 with 1 N HCl. The acidified solution is extracted with ethyl acetate and the organic layer is washed with satd. NaCl and evaporated to dryness. Crystallization of the crude material from ethylacetate/hexane affords pure compound as determined by analytical HPLC.

If a suitable benzoyl chloride or anhydride is not available then the corresponding substituted benzoic acid (100 mmols) is used in combination with HBTU or other amide coupling reagent. If this route is employed, 100 mmols of (L)-tyrosine or similar tyrosine analog is dissolved in 250 mL of dimethylformamide. In a separate vessel, the appropriate benzoic acid (110 mmols) in DMF is mixed with 110 mmols of HBTU or other amide coupling agent and 300 mmols of triethylamine or other weak base (NMM, DIPEA etc.). The mixture is allowed to stand for 10 minutes and then added to the tyrosine in one portion. After stirring for 1 hour at room temperature, the reaction mixture is concentrated under high vacuum and resuspended in ethyl acetate. The suspension is washed with 1 N HCL, water and satd. NaCl and evaporated to dryness. Crystallization affords pure compound.

A solution of thiophosgene (2 mmol) in 100 mL of dichloromethane is cooled to −78 deg under N$_2$. In a separate flask, N-substituted tyrosine intermediate (1 mmol) is dissolved in 20 mL of dichloromethane and diisopropylethylamine (2 mmol) is added. The resulting mixture is added drop wise to the cooled thiophosgene via a syringe. The reaction is allowed to warm to room temp. and is stirred 2h. The solvent is then evaporated to dryness and the residue recrystallized from ethyl acetate/hexaneto afford thiochloroformate.

The thiochloroformate intermediate (1 mmol) is dissolved in dichloromethane (100 mL) and 2 mmol of morpholine or other organic amine is added. The reaction is stirred for 1 h at room temp. and evaporated to dryness. The residue is dissolved in 1:1 acetonitrile/water and the thiocarbamate ester product purified by reverse phase HPLC (acetonitrile/water/0.1% trifluoroacetic acid).

The free alpha carboxylic acid may be converted to an ester or to an amide using reactions well known in the art. For example, a free carboxyl group can be reacted with a suitable alcohol in the presence of an acid to esterify the carboxyl group using well known reactions and reagents. Similarly, amides are formed by reacting the carboxylic acid with an amine with removal of the water produced by the condensation using known methods. A example of a reaction for esterification is shown below.

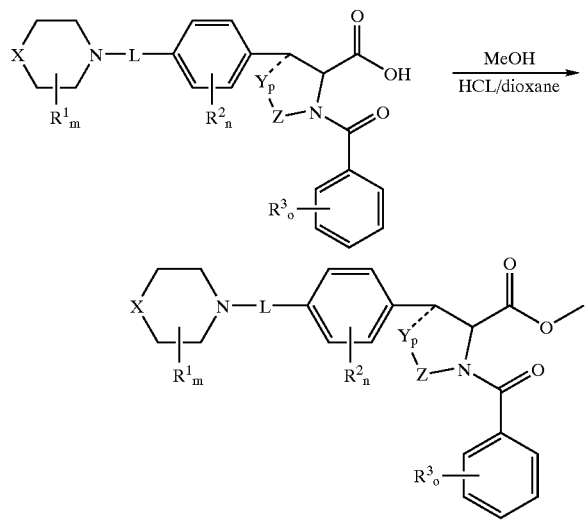

Compounds of formula I in which L is —C(O)—S— may be prepared by various routes using standard organic synthetic techniques from reagents that are commercially available. In a particular scheme, such compounds are synthesized in a similar manner to a carbamate starting with 4-thiophenyl alanine amino acid analogs according to the following scheme

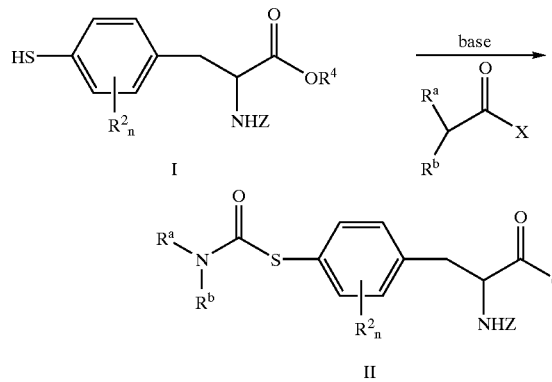

in which the 5-thiophenyl alanine compound is reacted with $R^aR^bN$—C(O)X and excess base such as TEA, DIPEA, NMM, $HCO_3$— and OH—.

Alpha-4 Inhibition

The compounds of the invention inhibit the binding of alpha-4 integrins to their ligands, in particular alpha4beta1 and alpha4beta7 on lymphocytes, eosinophiles, basophiles and monocytes to a cell expressing VCAM-1 and/or MAdCAM on the cell surface. The inhibitory compounds of the invention are useful to prevent the interaction of an epithelial cell bearing VCAM-1 and/or MAdCAM on the cell surface with a leukocyte cell bearing alpha4beta1 and/or alpha4beta7 on the surface by contacting the epithelial cell or the leukocyte with an inhibitory amount of the compound of the invention. The compounds are useful in assays to determine the inhibitory effect of a compound which antagonizes the binding of alpha4beta1 and/or alpha4beta7 integrin to VCAM-1 ligand and/or MAdCAM ligand. The inhibitory compound may be a small molecule, a protein or peptide or an antibody. In an in vitro assay, the ligand or the integrin may be directly or indirectly bound to a surface, such as microtiter plate, using known methods described for example in WO 9820110, WO 9413312, WO 9624673, WO 9806248, WO 9936393, and WO 9910312. The other member of the binding pair, e.g. the integrin or the ligand, respectively, (or a cell expressing the same on its surface) is then added to the surface bound member and the inhibitory effect of a test molecule is determined. The inhibitory activity of the compounds of the invention can also be determined with this type of assay.

The binding of the integrins to their respective ligands is known to be involved in inflammatory conditions associated with leukocyte infiltration of tissues lined with epithelial cells expressing VCAM-1 or MAdCAM. Such tissues include the gastrointestinal tract, skin, urinary tract, respiratory airways and joint synovial tissues. The compounds of the invention are useful in treating diseases in which such binding is implicated as a cause of the disease or symptoms of the disease. Undesired disease symptoms may arise from cell adhesin and/or cell activation which releases proinflammatory mediators, typically when there is an increase or upregulation in the expression of VCAM-1 and/or MAdCAM on the surface of endothelial cells. Various disease states which can be treated and for which the inflammatory symptoms can be reduced upon administration of the compounds of the invention include rheumatoid arthritis, asthma, psoriasis, multiple sclerosis, inflammatory bowel disease including ulcerative colitis, pouchitis and Crohn's disease, Celiac disease, nontropical Sprue, graft-versus-host disease, pancreatitis, insulin-dependent diabetes mellitus, mastitis, cholecystitis, pericholangitis, chronic sinusitis, chronic bronchitis, pneumonitis, collagen disease, eczema, and systemic lupus erythematosis. The compounds of the invention are useful in treating these diseases and conditions by inhibiting the integrin/ligand binding.

The compounds of the invention can be assayed for ability to block the alpha4beta7/MAdCAM-1 or alpha4beta1/VCAM-1 binding interaction by addition of serial dilutions of the samples to plates with the receptors as follows. 96-well plates are coated with mouse anti-human alpha-4 (31470D, PharMingen, San Diego, Calif.). The plates are decanted and blocked with 0.5% BSA. After washing $alpha_4beta_7$ or $alpha_4beta_1$ is added, followed by incubation for 2 h at room temperature. The plates are washed and samples of the small molecule antagonists are added to the plates with MAdCAM-1-Ig-HRP or VCAM-1-Ig-HRP for 2 h at room temperature. After an additional wash, the bound MAdCAM-1-Ig-HRP or VCAM-1-Ig-HRP is detected by addition of tetramethylbenzidine (TMB, Kirkegaard & Perry, Gaithersberg, Md.), followed by detection of the absorbance of the product.

Alternatively, the compounds can be assayed using any known protein-protein or cell-based assay method, such as those described, for example, in WO 99/10312 (examples 179–180) and WO 99/36393 (RPMI-CS-1 cell adhesion assay); Cardarelli et al., 1994, J. Biol. Chem., 269:18668–18673; and Viney et al, J. Immunol., 1996, 157: 2488–2497 (cell adhesion assay).

For example, 96-well ELISA plates are coated overnight at 4° C. with 2 µg/ml with anti-human CD49d, (31470D, PharMingen, San Diego, Calif.) in phosphate buffered saline. The plates are decanted and blocked with assay buffer (50 mM Tris-HCl, pH 7.5, 150 mM NaCl, 1 mM $MnCl_2$, 0.05% Tween-20 and 0.5% BSA) at room temperature for one hour, with gentle shaking. The plates are washed three times (in 50 mM Tris-HCl, pH 7.5, 100 mM NaCl, 1 mM $MnCl_2$, 0.05% Tween-20) and 2 µg/ml of the desired integrin (Genentech, Inc.) in assay buffer is added, followed by incubation at room temperature for two hours, with gentle shaking. After washing three times, 50 µl of samples of the small molecule antagonists (serial dilutions from 10 mM stocks in 100% DMSO) are added to the plates with 50 µl of 1 µg/ml MAdCAM-1-Ig-HRP or VCAM-1-Ig-HRP (Genentech, Inc) in assay buffer. The plates are incubated two hours at room temperature, with gentle shaking, followed by washing six times. The bound MAdCAM-1-Ig-HRP or VCAM-1-Ig-HRP is detected by addition of the peroxidase substrate, 3,3',5,5',tetramethylbenzidine (TMB, Kirkegaard & Perry, Gaithersberg, Md.), for 10 minutes, followed by addition of 1M phosphoric acid to stop the reaction. The absorbance of the solutions are read at 450 nm on a plate reader.

Suitable animal models exist for many diseases and conditions which can be treated with the compounds of the invention. Additional confirmation of the efficacy of these compounds in specific diseases and at desired doses can be assayed using these established models. For example, animal models of chronic inflammatory diseases such as asthma (Laberge, S. et al., Am. J. Respir. Crit. Care Med., 1995, 151:822–829.), rheumatoid arthritis (RA; Barbadillo, C. et al., Springer Semin. Immunopathol., 1995, 16:375–379), colitis (Viney et al, J. Immunol., 1996, 157: 2488–2497) and inflammatory bowel diseases (IBD; Podalski, D. K., N. Eng. J. Med., 1991, 325:928–937; Powrie, F. et al., Ther. Immunol., 1995, 2:115–123) may be used to demonstrate the activity of the compounds of the invention and to conduct dose and efficacy studies.

The invention also includes pharmaceutical compositions or medicaments containing the compounds of the invention and a therapeutically inert carrier, diluent or excipient, as well as methods of using the compounds of the invention to prepare such compositions and medicaments. Typically, the inhibitors used in the method of this invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to prevent, ameliorate, or treat the alpha-4 mediated disorder. Such amount is preferably below the amount that is toxic to the host or renders the host significantly more susceptible to severe infection.

As a general proposition, the initial pharmaceutically effective amount of the inhibitor administered parenterally per dose will be in the range of about 0.01–100 mg/kg, preferably about 0.1 to 20 mg/kg of patient body weight per day, with the typical initial range of compound used being 0.3 to 15 mg/kg/day. Oral unit dosage forms, such as tablets and capsules, preferably contain from about 25 to about 1000 mg of the compound of the invention.

The compound of the invention may be administered by any suitable means, including oral, opical, transdermal, parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration.

An example of a suitable oral dosage form is a tablet containing 25 mg, 50 mg, 100 mg, 250 mg, or 500 mg of the compound of the invention compounded with about 90–30 mg anhydrous lactose, about 5–40 mg sodium croscarmellose, about 5–30 mg polyvinylpyrrolidone (PVP) K30, and about 1–10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5–400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

EXAMPLES

The invention will be more fully understood by reference to the following examples. They should not, however, be construed as limiting the scope of the invention. All patent and literature citations are herein incorporated by reference in their entirety.

Example 1

Morpholino-thiocarbamate Inhibitor

Synthesis of N-(2-chlorobenzoyl)-(L)-tyrosine ethyl ester (2)

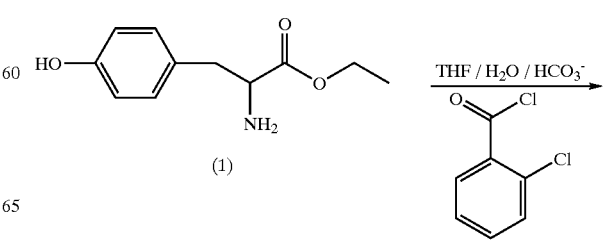

-continued

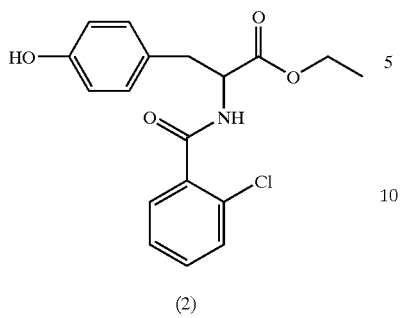

(2)

-continued

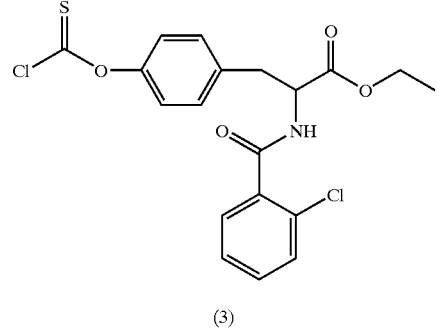

(3)

Into a 2L round bottom flask was added 21 g (100 mmol) of (L)-tyrosine ethyl ester (1) (Bachem) and 500 mL of tetrahydrofuran (THF). The mixture was magnetically stirred at room temperature until dissolved, and 500 mL of aqueous $NaHCO_3$ (0.5 M) was added. The mixture was cooled in an ice bath and 19.3 g (110 mmol) of 2-chlorobenzoyl chloride (Aldrich) was added slowly via a glass syringe. The ice bath was removed and the reaction was allowed to warm to room temperature with stirring. After 30 min., the reaction mixture was rotory evaporated under reduced pressure to remove the THF and the remaining aqueous bicarbonate solution was extracted twice with 400 mL ethyl acetate. The combined extracts were washed with 400 mL of satd. aqueous $NaHCO_3$, 400 mL of 0.1 N HCl, 400 mL of water, and 400 mL of satd. aqueous NaCl. The remaining organic layer was dried over $Na_2SO_4$ and evaporated to dryness to afford ~40 g of crude (2) as a pale yellow oil. The crude product (2) was recrystallized from ~800 mL of boiling ethyl acetate/hexane (~1:3) and cooled to 4° C. overnight. The resulting crystalline product was filtered and dried under a stream of nitrogen to afford 32 g (92% isolated yield) of purified (2). The N-(2-chlorobenzoyl)-(L)-tyrosine ethyl ester product (2) was confirmed by NMR and electrospray mass spectrometry (see attached) and judged >95% pure by HPLC and TLC ($R_f$=0.6, 1:1 ethyl acetate/hexane). The remaining 5% impurity (Rf=0.7) was identified as 2-chlorobenzoic acid by HPLC and TLC versus authentic material.

Synthesis of Thiochloroformate Intermediate (3)

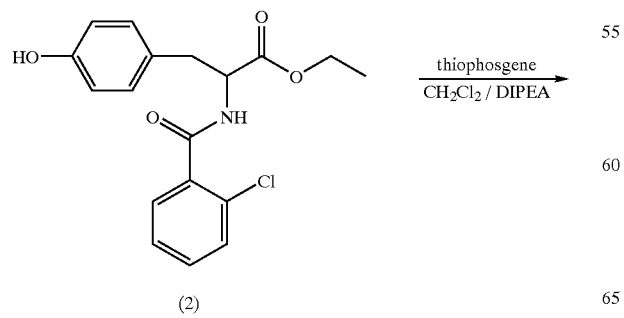

(2)

A solution of thiophosgene (2 mmol) in 100 mL of dichloromethane was cooled to −78 deg under $N_2$. In a separate flask, N-(2-chlorobenzoyl)-(L)-tyrosine ethyl ester (2) (1 mmol) was dissolved in 20 mL of dichloromethane and diisopropylethylamine DIPEA (2 mmol) was added. The resulting mixture was added drop wise to the cooled thiophosgene via a syringe. The reaction was allowed to warm to room temp. and stirred 2 h. The solvent was evaporated to dryness and the residue recrystallized from ethyl acetate/hexane to afford thiochloroformate (3).

Synthesis of Thiocarbamate Ethyl Ester (4)

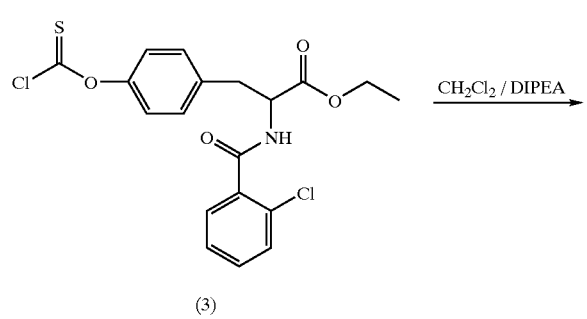

(3)

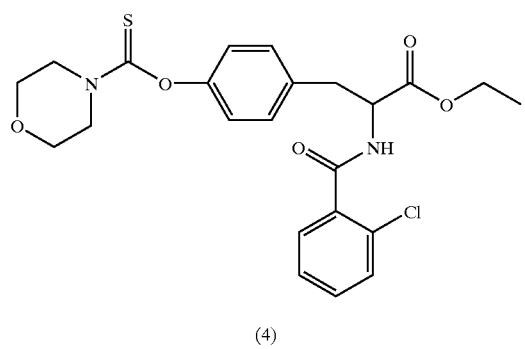

(4)

Thiochloroformate intermediate (3) (1 mmol) was dissolved in dichloromethane (100 mL) and 2 mmol of morpholine or other organic amine was added. The reaction was stirred for 1 h at room temp. and evaporated to dryness. The residue was dissolved in 1:1 acetonitrile/water and the thiocarbamate ethyl ester product purified by reverse phase HPLC (acetonitrile/water/0.1% trifluoroacetic acid).

Synthesis of Morpholino-thiocarbamate 5

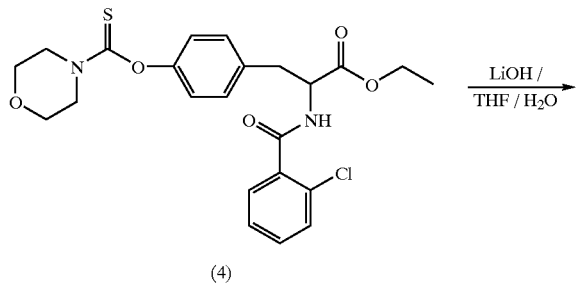

(4)

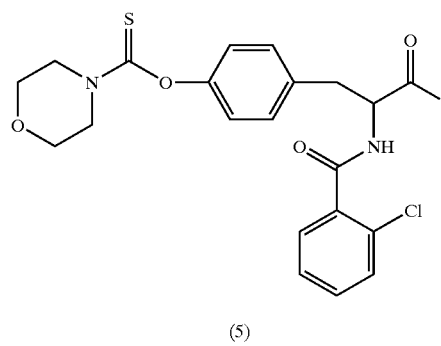

(5)

Into a round bottom flask with a magnetic stirrer was added (0.65 mmol) of (4) (from above) and 30 mL THF. The mixture was stirred until dissolved and 20 mL of $H_2O$ was added followed by 1 mL of aqueous 1M LiOH (1 mmol). The resulting suspension was stirred vigorously at room temperature for 2 h or until TLC (5% $CH_3CO_2H$ in ethyl acetate) indicated complete disappearance of starting material. The reaction mixture was acidified to pH<3 via addition of 0.1 M aqueous HCl and concentrated via rotory evaporation to remove most of the THF. The resulting aqueous suspension was extracted 2x with 40 mL of ethyl acetate. The combined organic extracts were dried over $Na_2SO_4$ and rotory evaporated to afford crude (5). The crude product was recrystallized from ethyl acetate/hexane (~2:1) and cooled to 4 deg. overnight. The crystalline product was filtered and dried under a stream of nitrogen to afford morpholino-thiocarbamate product (5) as a pale yellow solid.

In a similar manner compounds were produced in which morpholine was substituted with piperidine, piperazine and N-acetyl-piperazine.

Example 2

Pharmacokinetic Properties and Activity

Clearance and Half Life

Jugular Vein Cannulation—Animals are anesthetized via IP injection using Ketamine/Xylazine/saline solution (@ 0.25 mL/kg). Animals are weighed prior to dosing of anesthetic to determine proper dosage. Sterile instruments and aseptic technique are used throughout surgery. This includes wearing a mask, clean lab coat or scrubs and sterile gloves. The ventral and dorsal neck areas are shaved and prepped with betadine and alcohol. A small skin incision is made over the jugular vein. Using blunt dissection techniques, free the intended vessel from surrounding tissue and thread two sutures under the vein. Tie the cranial suture, nick the vessel, insert the catheter, and use the distal suture to secure the catheter. Dissect a subcutaneous passage between the catheter insertion point and the intrascapular space; make a small exit hole at the nape of the neck. Then, using hemastats, pull the cannula through the passage to the dorsal neck area. Confirm that the catheter is still properly placed, flush with appropriate heparin/saline solution, and knot the distal end of the cannula. Place a suture tie around the knot, coil the cannula under the skin and close the dorsal incision, leaving the "tie" slightly exposed for ease of externalizing the catheter. Close the ventral incision. The animal should be recovered on a circulating heating blanket or equivalent and returned to its room when it's able to right itself.

Test Articles

Compounds are formulated with polyethylene glycol 400 (PEG) at 30% (IV) or 60% (PO).

Dose Administration

Intravenous (IV) dosing is accomplished with a bolus injection into a lateral tail vein. Animals are restrained using a rat restrainer to minimize mis-dosings and to reduce animal stress. Individual doses are calculated based on body weights taken the morning of the dose. Oral (PO) dosing is accomplished by oral gavage using a 3½ inch stainless steel animal feeding tube. Animals are restrained by grasping gently with our hands to reduce animal stress. Individual doses are calculated based on body weights taken the morning of the dose.

Blood Sample Collection

Blood (approximately 0.2 mL) is collected from an jugular cannula. For occasions when the jugular cannula fails, blood is removed from the remaining lateral tail vein. The whole blood was placed into Microtainer® tubes containing $K_2EDTA$ anticoagulant. Samples are inverted several times to ensure proper mixing with anticoagulant and are stored on ice until centrifugation. Samples are centrifuged at 10,000×g for 5 minutes and plasma is transferred to 1.5 mL microcentrifuge tube. Blood samples, for IV dose administrations are collected prior to the dose administration (predose) and at 2, 5, 10, 20, 30, 45, 60, 120 minutes, 4, 6, 8 and 10 hours postdose of the dose administration. For PO dose administration, the blood collection time points are the same as IV dose administration, except no blood sample is collected at 2 minutes.

All plasma samples are measured by LC/MS/MS. All pharmacokinetic parameters, clearance (CL), half life (t½), area under curve (AUC) and maximum conc (Cmax) are determined using WinNonin (version 3.2).

TABLE 1

| compound | | Assay Result | |
|---|---|---|---|
| reference carbamate | 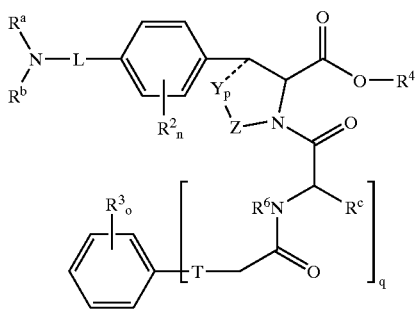 | Cl (ml/min/kg)<br>AUCmet/<br>AUCpar<br>T1/2 (min) | 50<br>0.96<br><br>6 |
| 1 | 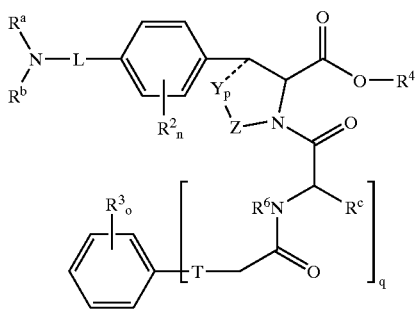 | Cl (ml/min/kg)<br>AUCmet/<br>AUCpar<br>T1/2 (min) | 23<br>0.04<br><br>61 |

We claim:

1. A compound of formula I:

I wherein q is 0 or 1;

T is O, $CHR^6$, $NR^6$, S, SO, $SO_2$, —$NR^6C(O)$—, —$C(O)NR^6$—;

$R^a$ and $R^b$ are each independently hydrogen, alkyl, alkoxy, a carbocycle, a heterocycle, optionally substituted with halogen, hydroxy, amino, carboxyl, nitro, cyano, a carbocycle or a heterocycle; and one to three carbon atoms of said alkyl and alkoxy groups are optionally replaced with carbonyl, $NR^6$, O, S, SO or $SO_2$; or $R^a$ and $R^b$ together with the nitrogen to which they are attached may form a heterocycle or heteroaryl group substituted with 0–4 $R^1$ substituents;

$R^c$ is H, alkyl, optionally substituted with hydroxy, halogen, alkoxy, amino, a carbocycle or a heterocycle; and one to three carbon atoms of said alkyl are optionally replaced with carbonyl, $NR^6$, O, S, SO or $SO_2$;

L is —C(S)—O— or —C(O)—S—;

Y is $CH_2$ or absent when p is 0;

Z is H or lower alkyl, or when p is 1 then Z and Y together with the atoms from which they depend form a 5 member saturated or partially unsaturated 5 or 6 member heterocycle;

$R^1$ in each instance is independently selected from the group consisting of hydroxy, amino, amidine, guanidine, carboxyl, nitro, cyano, thiol, alkyl, alkoxy a carbocycle and a heterocycle wherein said alkyl and alkoxy groups are optionally substituted with one or more hydroxyl, halogen, amino, amidine, guanidine, carboxyl, nitro, cyano, carbocycle or heterocycle; and one to three carbon atoms of said alkyl and alkoxy groups are optionally replaced with carbonyl, $NR^6$, O, S, SO or $SO_2$; and said carbocycle and heterocycle group is optionally substituted with one or more hydroxyl, halogen, amino, amidine, guanidine carboxyl, nitro, cyano, alkyl, alkoxy or haloalkyl;

or two $R^1$ substituents together with the atoms from which they depend form a fused or bridged heterocycle optionally substituted with one or more hydroxyl, halogen, amino, amidine, guanidine carboxyl, nitro, cyano, alky, alkoxy or haloalkyl;

$R^2$ and $R^3$ in each instance are independently selected from the group consisting of hydroxy, amino, amidine, guanidine, carboxyl, nitro, cyano, thiol, alkyl, alkoxy, a carbocycle and a heterocycle wherein said alkyl and alkoxy groups are optionally substituted with one or more hydroxyl, halogen, amino, amidine, guanidine, carboxyl, nitro, cyano, alkoxy, carbocycle or heterocycle; and one to three carbon atoms of said alkyl group is optionally replaced with carbonyl, $NR^6$, O, S, SO or $SO_2$; and said carbocycle and heterocycle group is optionally substituted with one or more hydroxyl, halogen, amino, amidine, guanidine, carboxyl, nitro, cyano, alkyl, alkoxy or haloalkyl;

$R^4$ is H, alkyl, a carbocycle or heterocycle wherein said alkyl is optionally substituted with a carbocycle or heterocycle and said alkyl, carbocycle and heterocycle are optionally substituted with lower alkyl, halogen, hydroxyl, alkoxy, haloalkyl or amino;

R⁶ in each instance is independently H, alkyl or a carbocycle;

m, n, and o are each independently 0–4;

p is 0 or 1; and salts and solvates thereof.

2. A compound of the formula II:

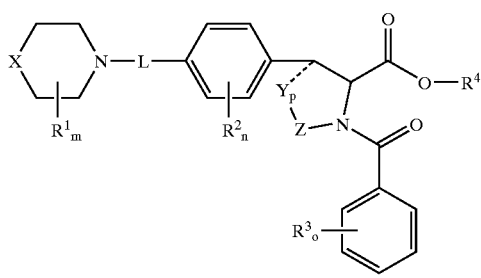

wherein

L is —C(S)—O— or —C(O)—S—;

X is O, NR⁵, CR¹R⁶, S, SO or SO₂;

Y is CH₂ or absent when p is 0;

Z is H or lower alkyl, or when p is 1 then Z and Y together with the atoms from which they depend form a 5 member saturated or partially unsaturated 5 or 6 member heterocycle;

R¹ in each instance is independently selected from the group consisting of hydroxy, amino, amidine, guanidine, carboxyl, nitro, cyano, thiol, alkyl, alkoxy a carbocycle and a heterocycle wherein said alkyl and alkoxy groups are optionally substituted with one or more hydroxyl, halogen, amino, amidine, guanidine, carboxyl, nitro, cyano, carbocycle or heterocycle; and one to three carbon atoms of said alkyl and alkoxy groups are optionally replaced with carbonyl, NR⁶, O, S, SO or SO₂; and said carbocycle and heterocycle group is optionally substituted with one or more hydroxyl, halogen, amino, amidine, guanidine carboxyl, nitro, cyano, alkyl, alkoxy or haloalkyl;

or two R¹ substituents together with the atoms from which they depend form a fused or bridged heterocycle optionally substituted with one or more hydroxyl, halogen, amino, amidine, guanidine carboxyl, nitro, cyano, alky, alkoxy or haloalkyl;

R² and R³ in each instance are independently selected from the group consisting of hydroxy, amino, amidine, guanidine, carboxyl, nitro, cyano, thiol, alkyl, alkoxy, a carbocycle and a heterocycle wherein said alkyl and alkoxy groups are optionally substituted with one or more hydroxyl, halogen, amino, amidine, guanidine, carboxyl, nitro, cyano, alkoxy, carbocycle or heterocycle; and one to three carbon atoms of said alkyl group is optionally replaced with carbonyl, NR⁶, O, S, SO or SO₂; and said carbocycle and heterocycle group is optionally substituted with one or more hydroxyl, halogen, amino, amidine, guanidine, carboxyl, nitro, cyano, alkyl, alkoxy or haloalkyl;

R⁴ is H, alkyl, a carbocycle or heterocycle wherein said alkyl is optionally substituted with a carbocycle or heterocycle and said alkyl, carbocycle and heterocycle are optionally substituted with lower alkyl, halogen, hydroxyl, alkoxy, haloalkyl or amino;

R⁵ in each instance is independently selected from the group consisting of H, alkyl, a carbocycle and a heterocycle wherein said alkyl group is optionally substituted with one or more hydroxyl, halogen, amino, amidine, guanidine, carboxyl, nitro, cyano, alkoxy carbocycle or heterocycle; and one to three carbon atoms of said alkyl group is optionally replaced with carbonyl, NR⁶, O, S, SO or SO₂; and said carbocycle and heterocycle group is optionally substituted with one or more hydroxyl, halogen, amino, amidine, guanidine carboxyl, nitro, cyano, alkyl, alkoxy or haloalkyl;

R⁶ in each instance is independently H, alkyl or a carbocycle;

m, n, and o are each independently 0–4;

p is 0 or 1; and salts and solvates thereof.

3. The compound of claim 2, wherein X is O.

4. The compound of claim 2, wherein Y is absent and p is 0 and Z is H or alkyl.

5. The compound of claim 2, wherein R¹ in each instance is H; or alkyl, aryl, heteroaryl each optionally substituted with hydroxyl, halogen amino or cyano; or two R¹ substituents together with the atoms from which they depend form a fused aryl group or bridged heterocycle optionally substituted with hydroxyl, halogen, amino, alky, alkoxy.

6. The compound of claim 2, wherein X is O and R¹ is H, methyl or ethyl; or two R¹ substituents together with the atoms from which they depend form a 2-Oxa-5-azabicyclo[2.2.1]heptane bridged heterocycle.

7. The compound of claim 2, wherein X is NR⁵ wherein R⁵ is H, alkyl, alkanoyl, optionally substituted with hydroxyl, halogen, amino or aryl.

8. The compound of claim 7, wherein two R¹ substituents together with the atoms from which they depend form a 2,5-Diazabicyclo[2.2.1]heptane bridged heterocycle.

9. The compound of claim 2, wherein R² in each instance is independently halogen, alkyl, alkoxy, aryl or aryloxy.

10. The compound of claim 9, wherein n is 1 and R² is adjacent to the thiocarbamate linkage and is selected from the group consisting of Cl, I, methyl, methoxy and phenyl.

11. The compound of claim 2, wherein R³ is halogen, nitro, carboxyl or alkylsulfonyl optionally substituted with halogen, hydroxyl or alkoxy.

12. The compound of claim 2, wherein R³ is Cl, nitro, carboxyl, —NHSO₂CF₃, —NHC(O)CF₃ or 4-methyl-phenyl.

13. The compound of claim 2, wherein R³ is Cl in the ortho position and o is 1.

14. The compound of claim 2, wherein R⁴ is H, alkyl or aralkyl.

15. The compound of claim 2, wherein R⁴ is H.

16. The compound of claim 1, wherein Rᵃ and Rᵇ together with the nitrogen atom from which they depend form a group selected from the group consisting of

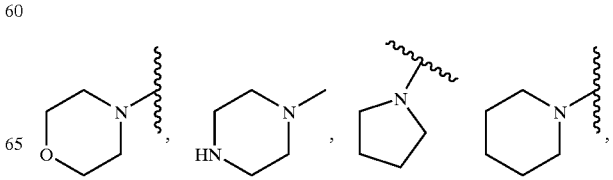

-continued
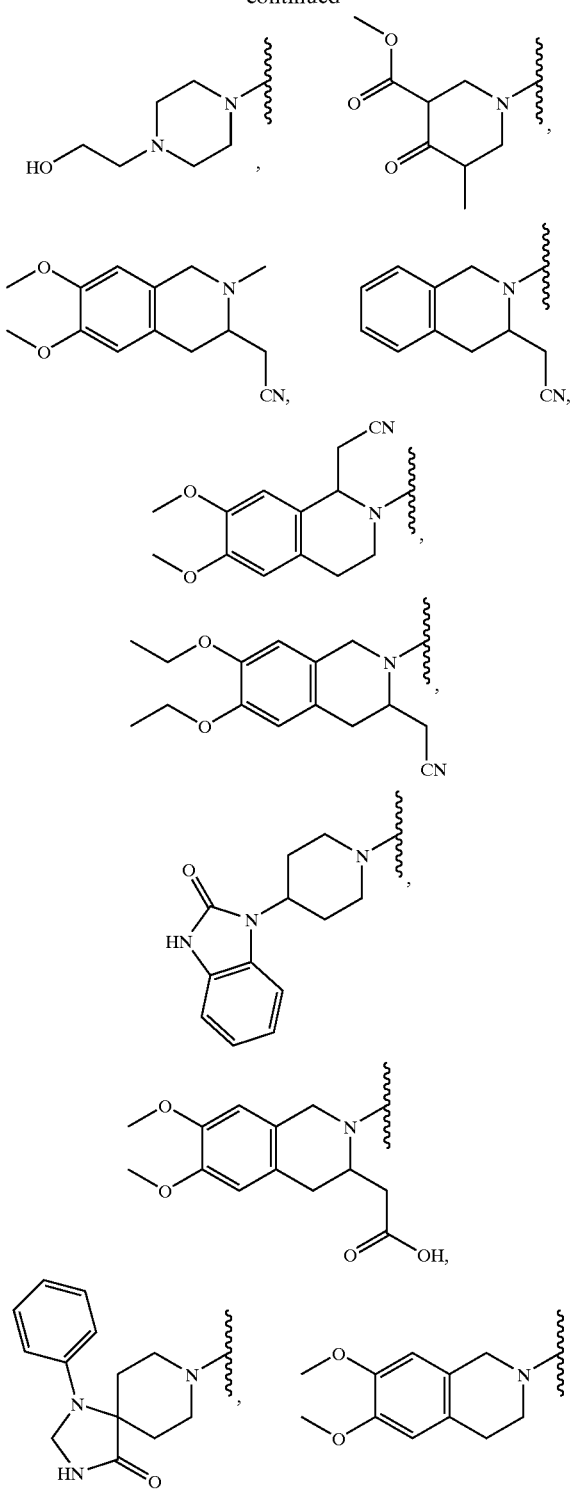
and
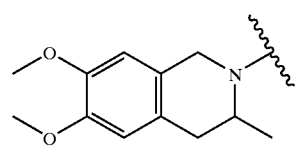
17. The compound of claim 1, wherein $R^a$ and $R^b$ together with the nitrogen atom from which they depend form a group selected from the group consisting of
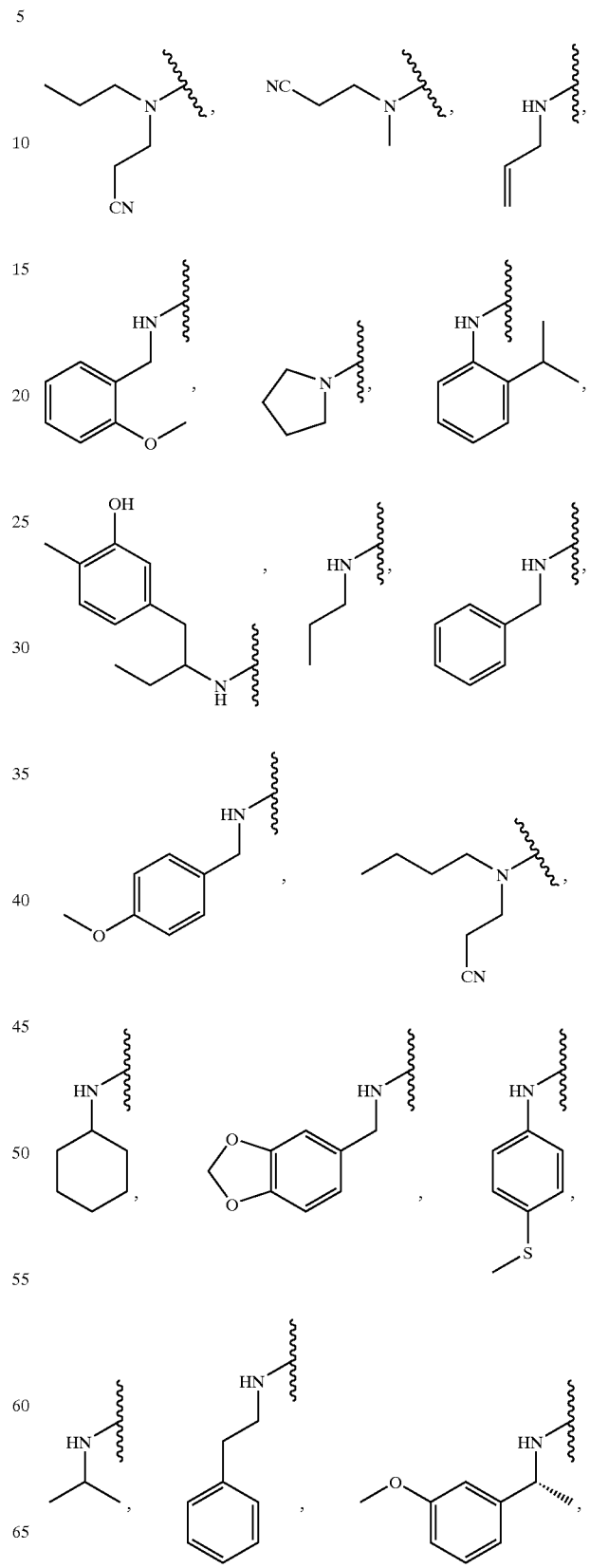

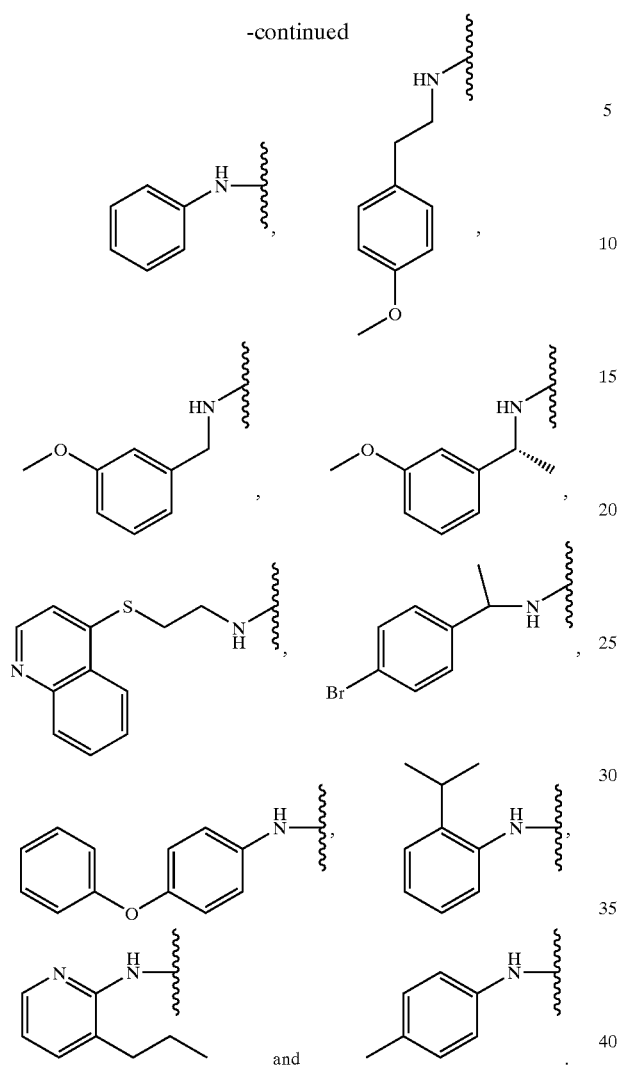
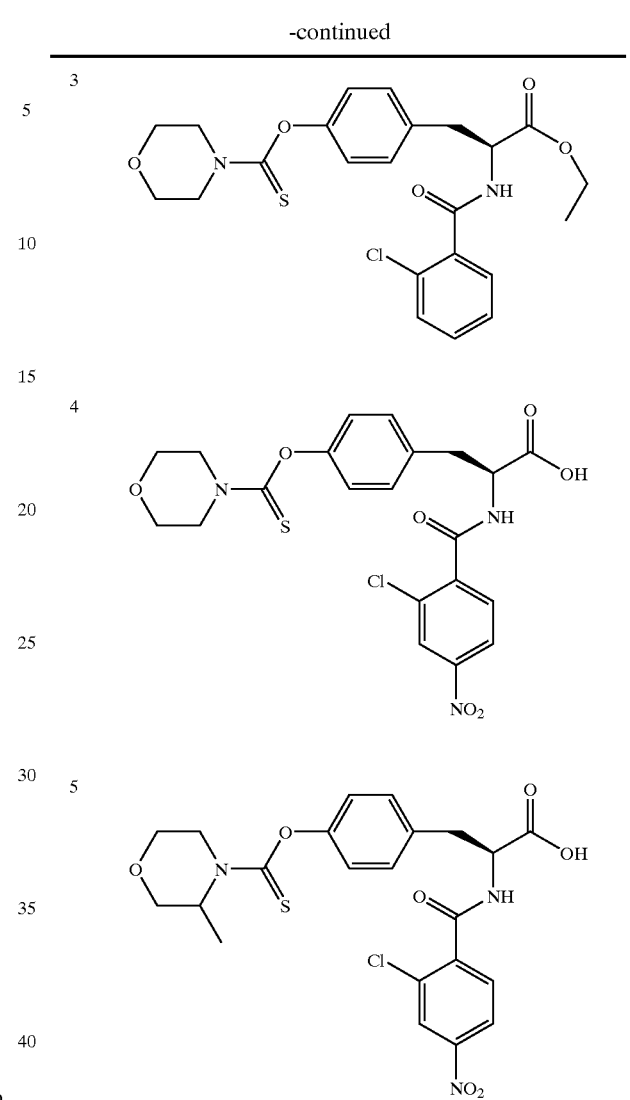
18. The compound of claim 2, selected from the group consisting of:
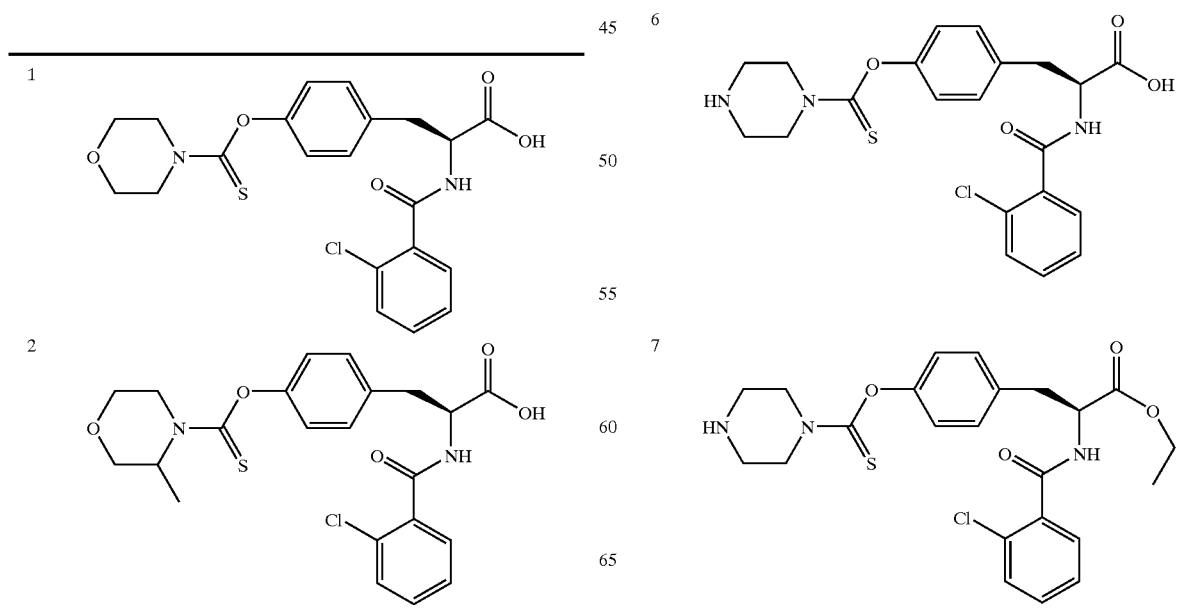

-continued
8
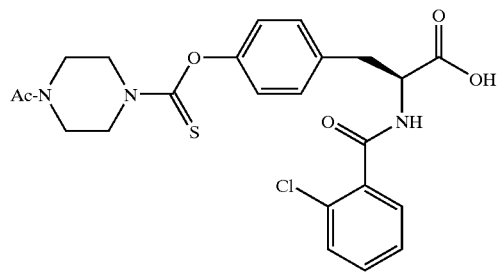
9
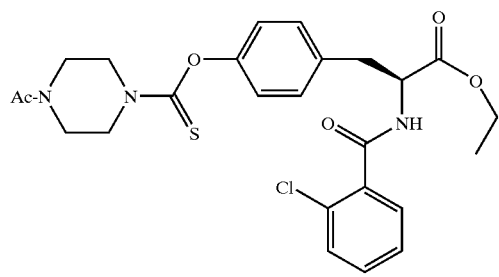
10
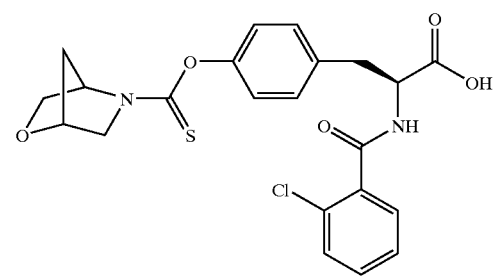
-continued
11
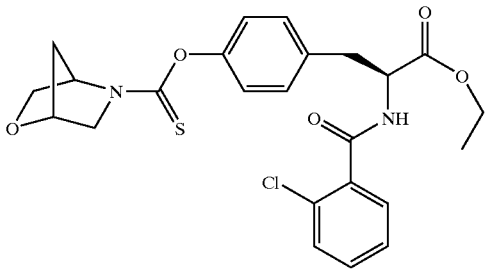
12
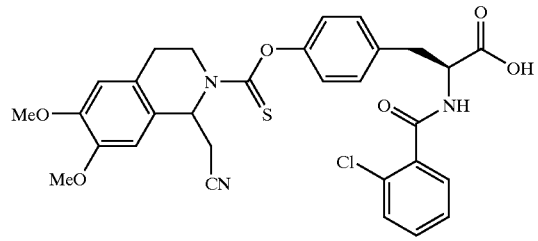
and
13
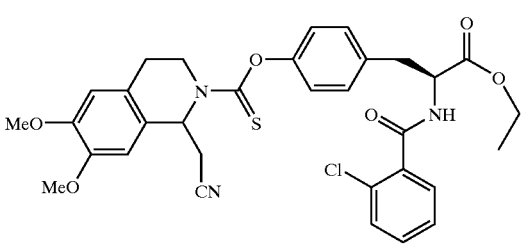
* * * * *